(12) United States Patent
Darnell et al.

(10) Patent No.: US 10,729,547 B2
(45) Date of Patent: Aug. 4, 2020

(54) IMPLANTABLE PENILE PROSTHESIS

(71) Applicant: Boston Scientific Scimed, Inc., Maple Grove, MN (US)

(72) Inventors: Ryan Darnell, Eden Prairie, MN (US); Robert J. Berkenes, Buffalo, MN (US); Robert L. Rykhus, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 116 days.

(21) Appl. No.: 15/989,919

(22) Filed: May 25, 2018

(65) Prior Publication Data

US 2018/0271656 A1  Sep. 27, 2018

Related U.S. Application Data

(63) Continuation of application No. 14/430,844, filed as application No. PCT/US2013/062131 on Sep. 27, 2013, now Pat. No. 9,999,508.

(60) Provisional application No. 61/706,468, filed on Sep. 27, 2012.

(51) Int. Cl.
*A61F 2/26* (2006.01)
*A61F 2/48* (2006.01)

(52) U.S. Cl.
CPC .......... *A61F 2/26* (2013.01); *A61F 2002/484* (2013.01); *A61F 2210/0071* (2013.01); *A61F 2230/0069* (2013.01); *F04C 2270/041* (2013.01)

(58) Field of Classification Search
CPC ........ A61H 19/00; A61H 19/30; A61H 19/32; A61H 19/34; A61H 19/50

USPC .................................................... 600/38–41
See application file for complete search history.

(56) References Cited

U.S. PATENT DOCUMENTS

| | | | |
|---|---|---|---|
| 3,954,102 A | | 5/1976 | Buuck |
| 4,267,829 A | * | 5/1981 | Burton ...................... A61F 2/26 600/40 |
| 4,353,360 A | * | 10/1982 | Finney ...................... A61F 2/26 600/40 |
| 4,424,807 A | | 1/1984 | Evans, Sr. |
| 4,550,720 A | | 11/1985 | Trick |
| 4,651,721 A | | 3/1987 | Mikulich et al. |
| 4,773,403 A | | 9/1988 | Daly |

(Continued)

FOREIGN PATENT DOCUMENTS

| | | |
|---|---|---|
| EP | 1265553 A2 | 12/2002 |
| WO | 2006096001 A1 | 9/2006 |

OTHER PUBLICATIONS

Extended European Search Report for European Application No. 18207667.9, dated Jun. 11, 2019, 8 pages.

(Continued)

*Primary Examiner* — Samuel G Gilbert
(74) *Attorney, Agent, or Firm* — Brake Hughes Bellermann LLP

(57) ABSTRACT

The present application is generally directed to an expandable sleeve component of an implantable penile prosthesis, to a prosthesis containing the sleeve, and to related methods of preparation and use. More specifically, the present application is directed to an implantable penile prosthesis having a cylindrical polymeric (e.g., extruded, molded, etc.) sleeve for controlling cylinder expansion upon placement of the prosthesis within a corpus cavemosum and expansion during use.

20 Claims, 21 Drawing Sheets

(56) References Cited

U.S. PATENT DOCUMENTS

| | | | |
|---|---|---|---|
| 4,881,530 A * | 11/1989 | Trick | A61F 2/26 |
| | | | 600/40 |
| 5,263,981 A | 11/1993 | Polyak et al. | |
| 6,346,492 B1 | 2/2002 | Koyfman | |
| 6,733,527 B2 | 5/2004 | Koyfman | |
| 6,929,599 B2 | 8/2005 | Westrum, Jr. | |
| 7,066,878 B2 | 6/2006 | Eid | |
| 7,169,103 B2 | 1/2007 | Ling et al. | |
| 7,491,164 B2 | 2/2009 | Choi et al. | |
| 2002/0033564 A1 | 3/2002 | Koyfman | |
| 2008/0139880 A1 | 6/2008 | Choi et al. | |
| 2009/0124851 A1 | 5/2009 | Kuyava et al. | |

OTHER PUBLICATIONS

Extended European Search Report for European Application 13842949.3, dated Jul. 11, 2016, 8 pages.

First Examination Report for Australian Application 20130323390, dated Mar. 20, 2017, 3 pages.

\* cited by examiner

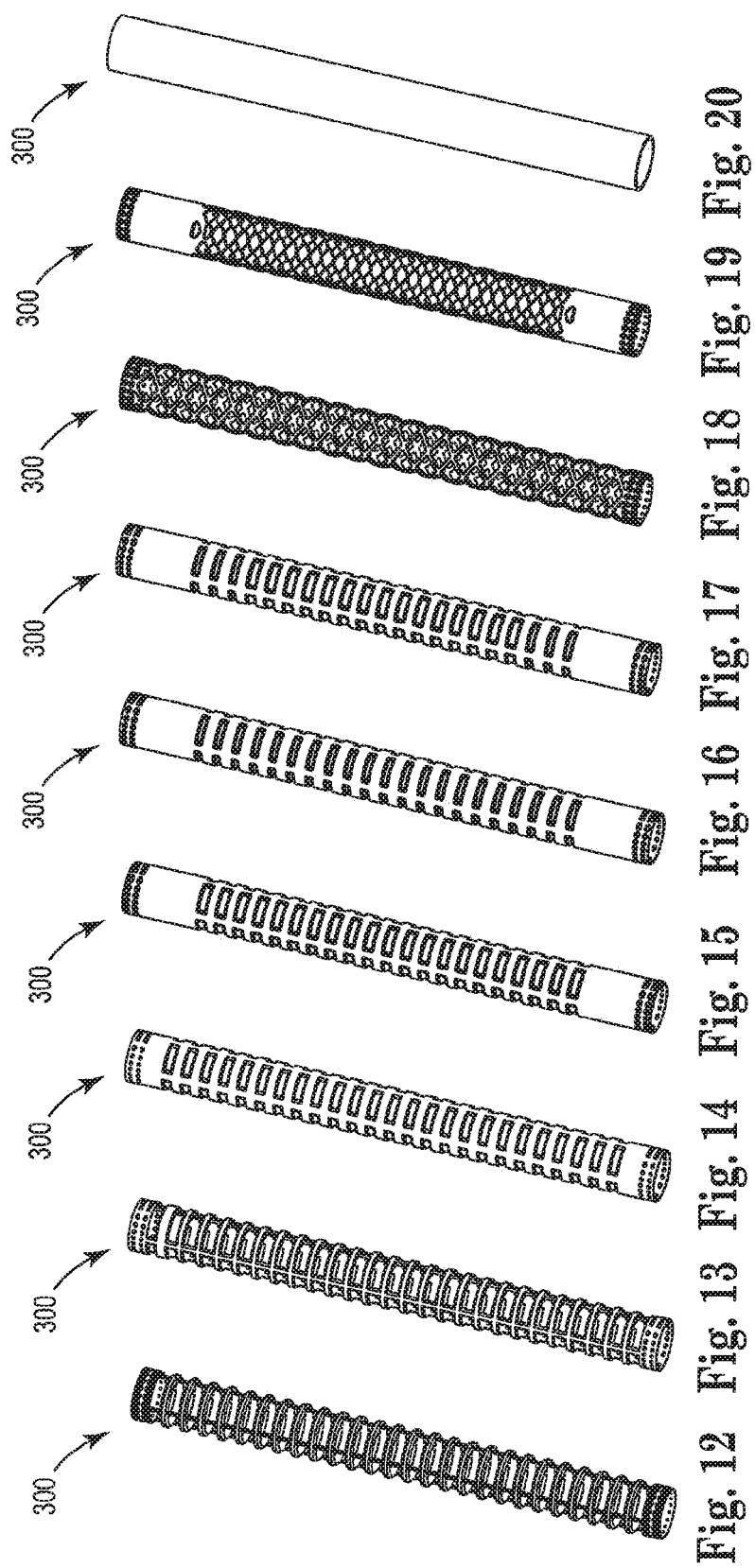

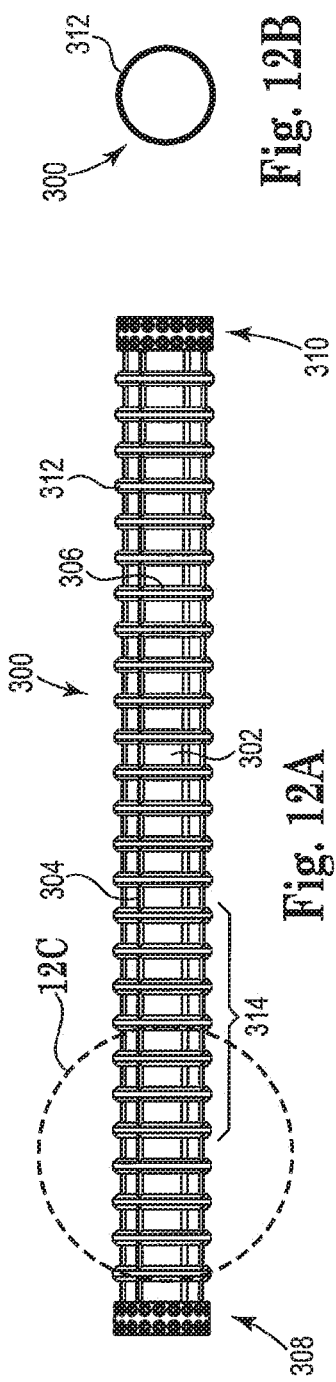

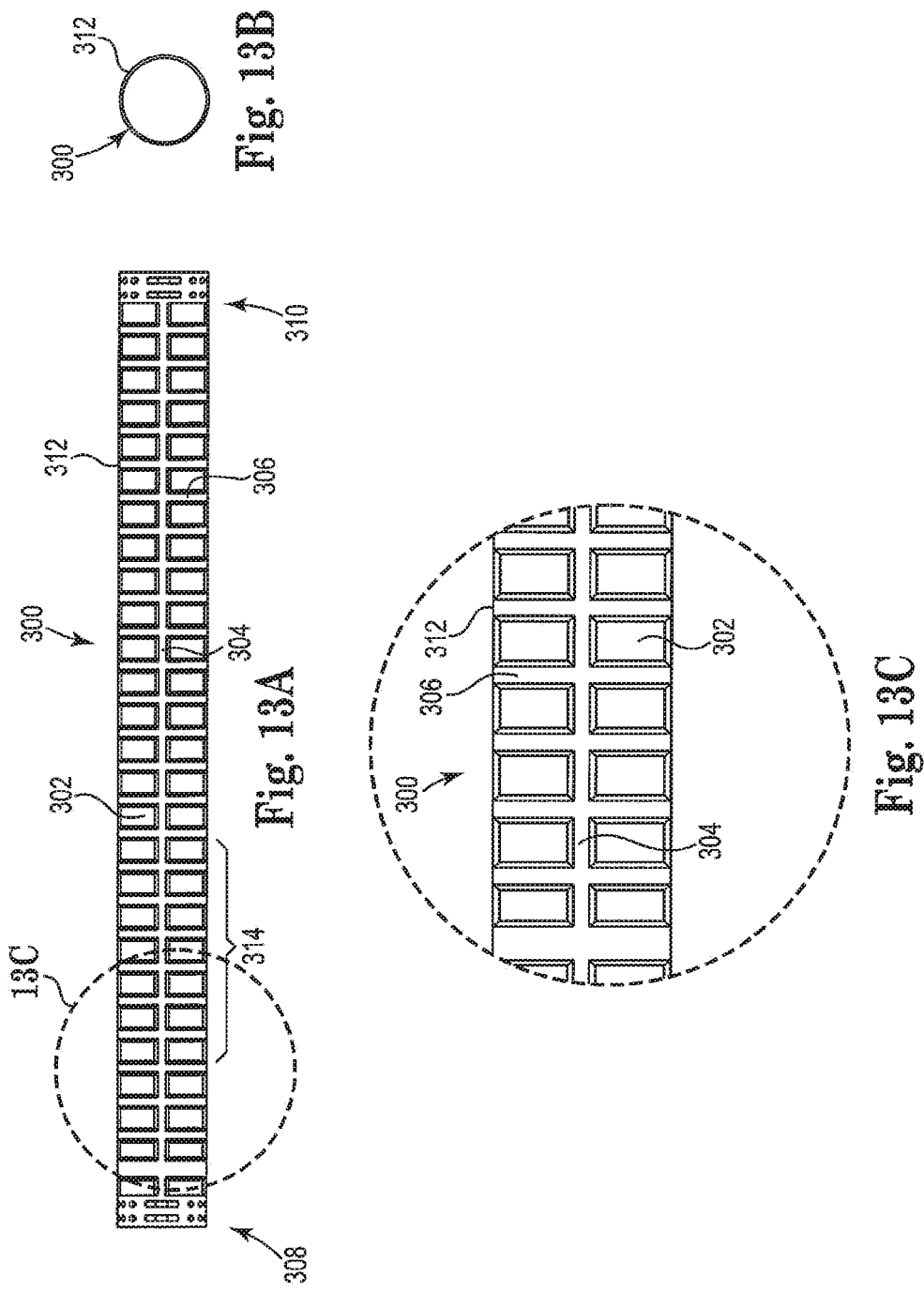

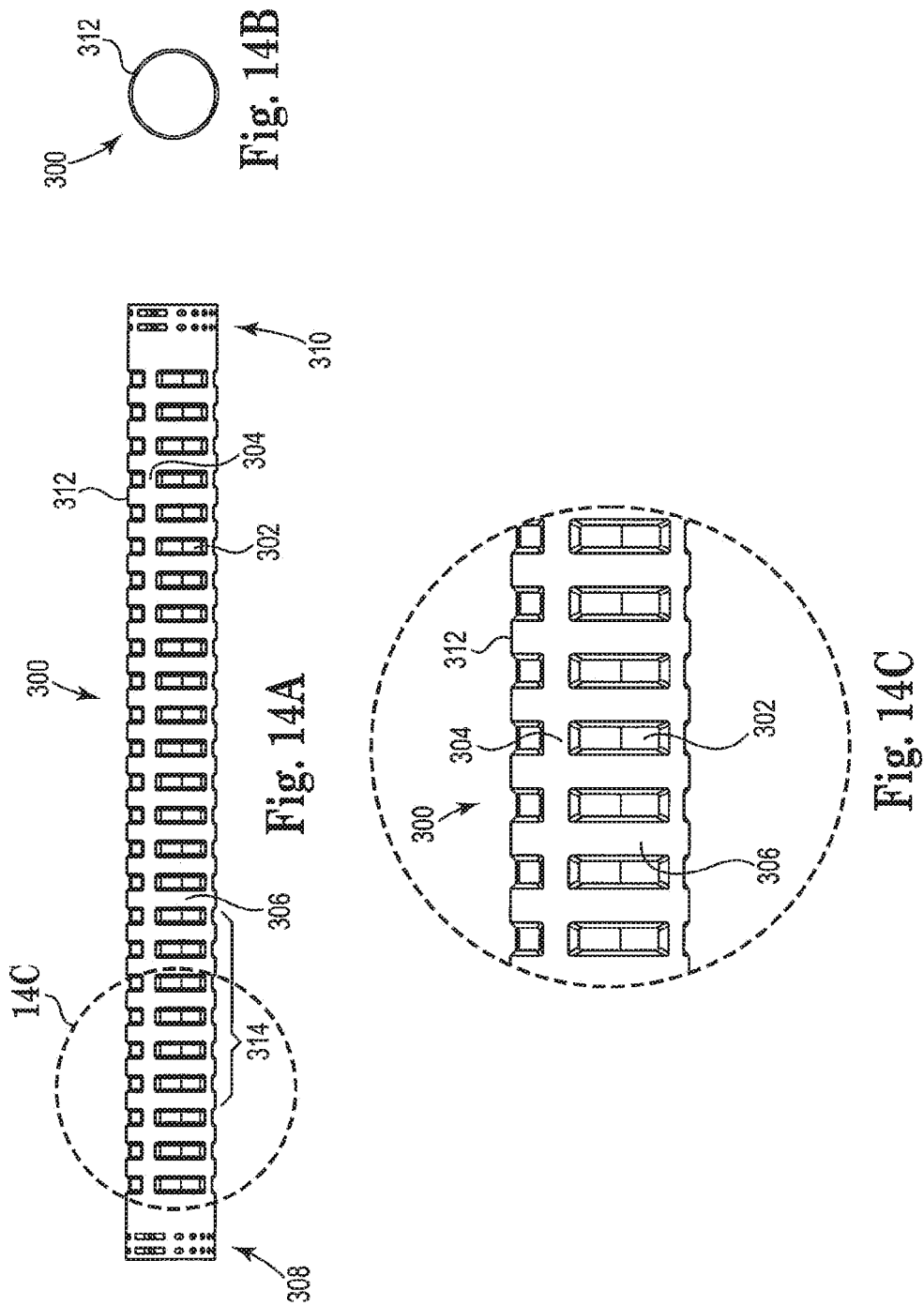

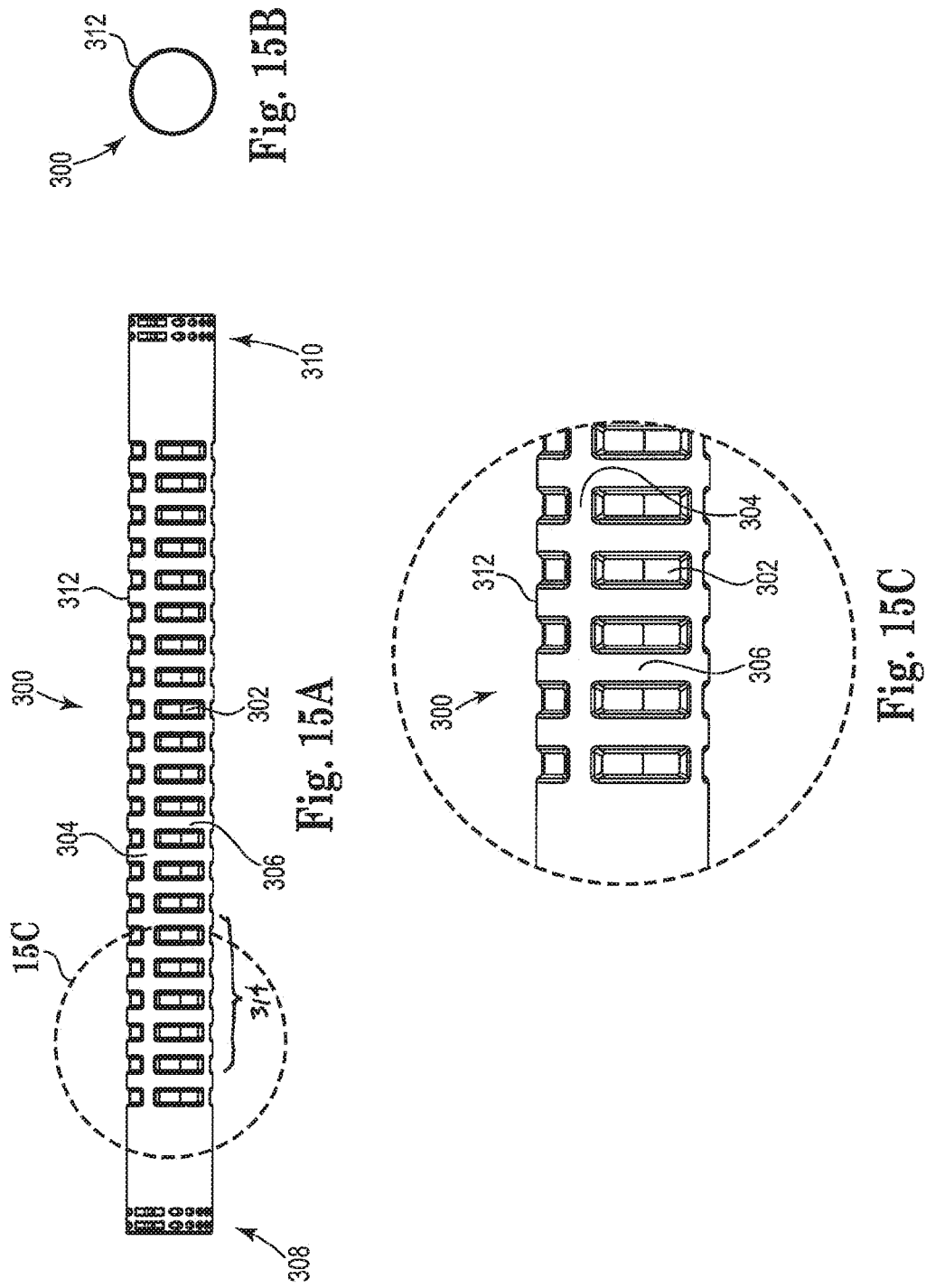

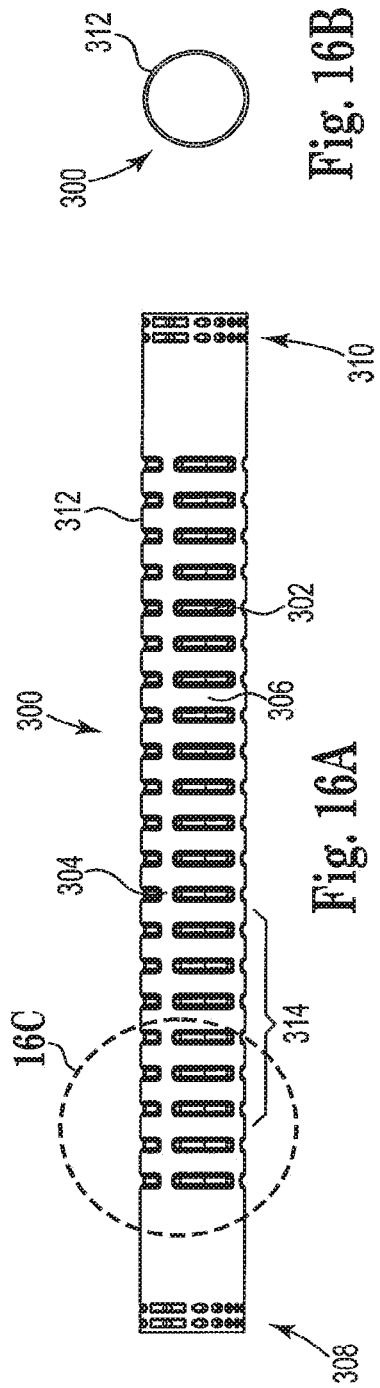

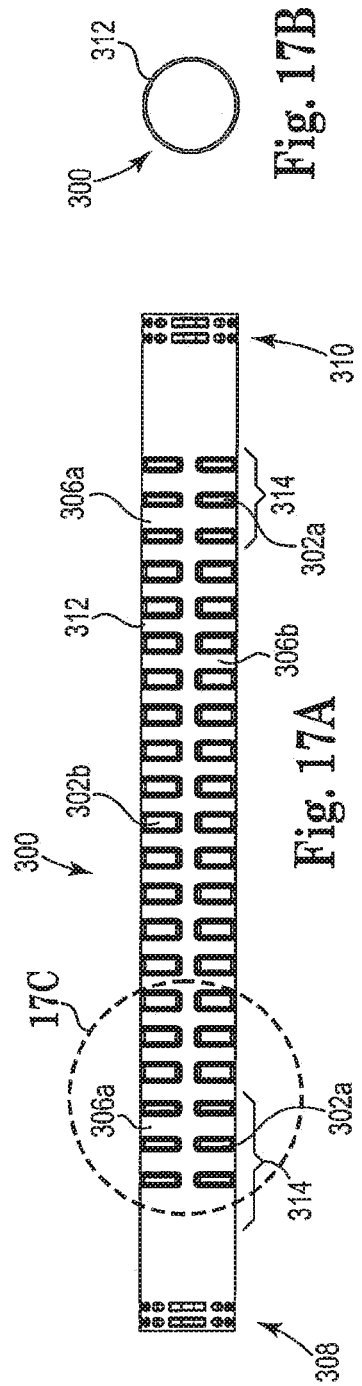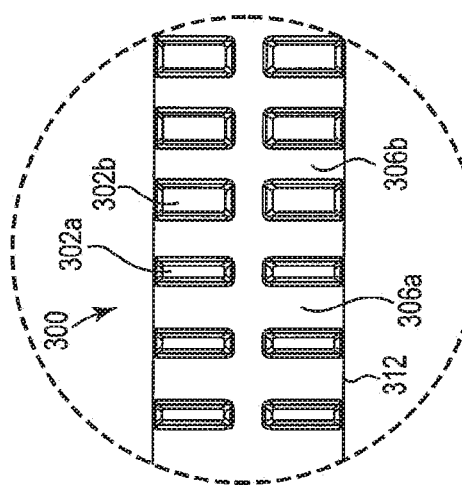

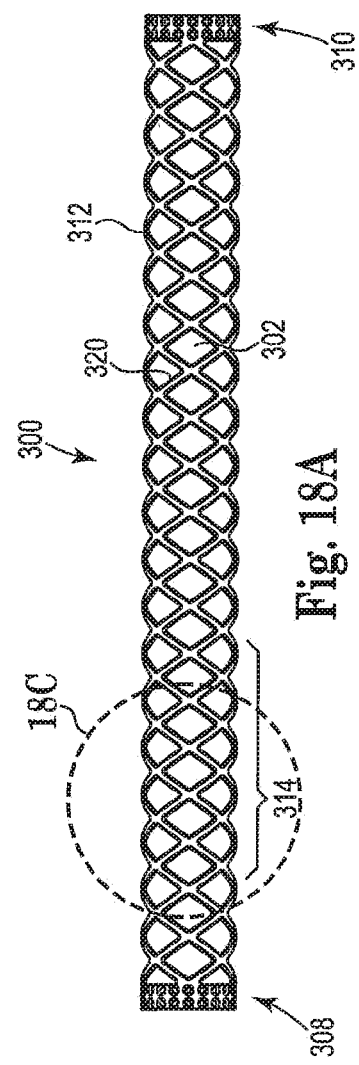
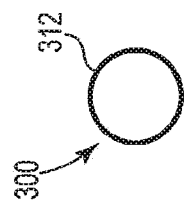
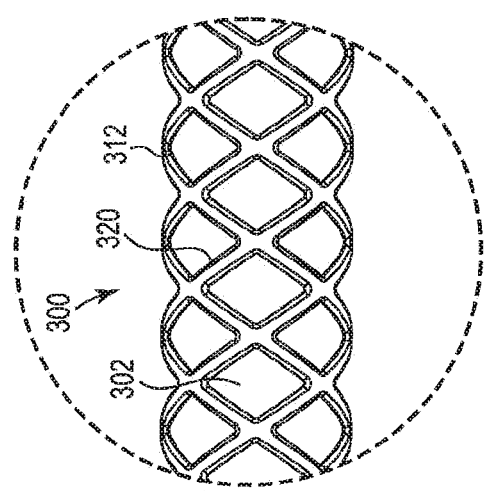

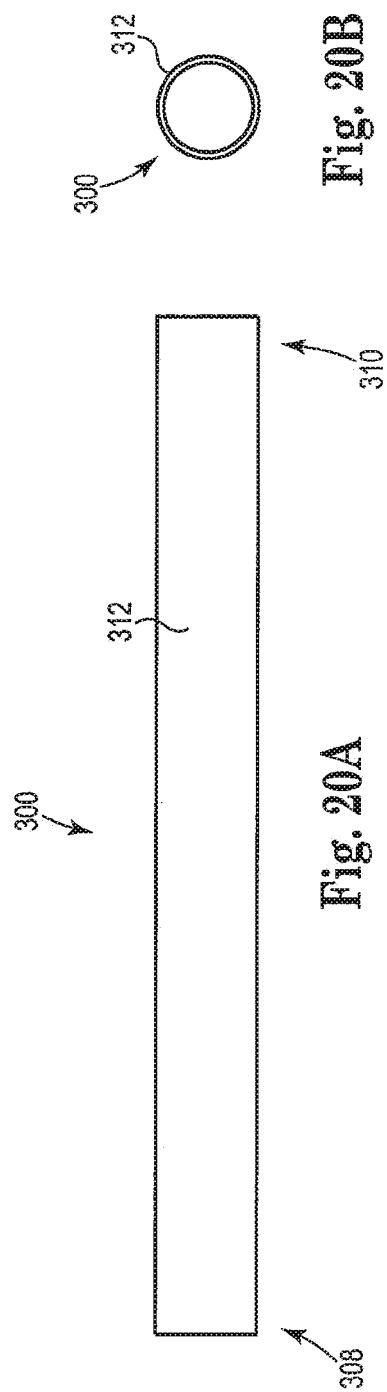

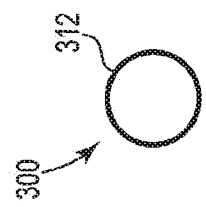
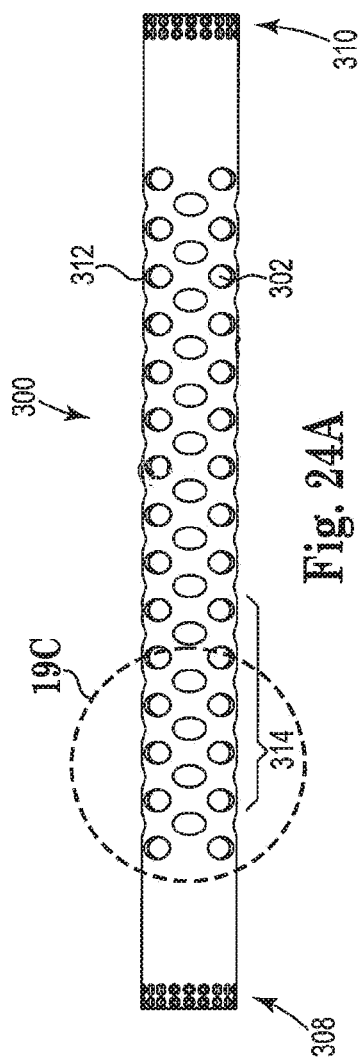
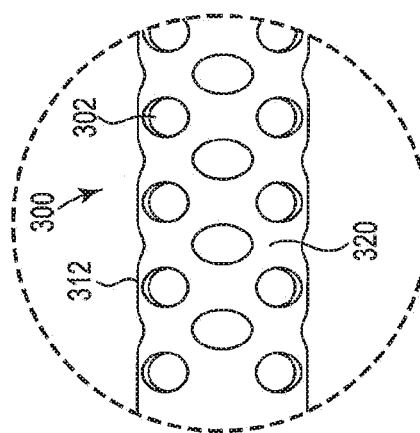

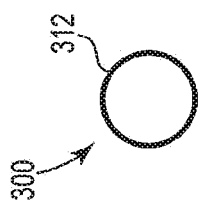
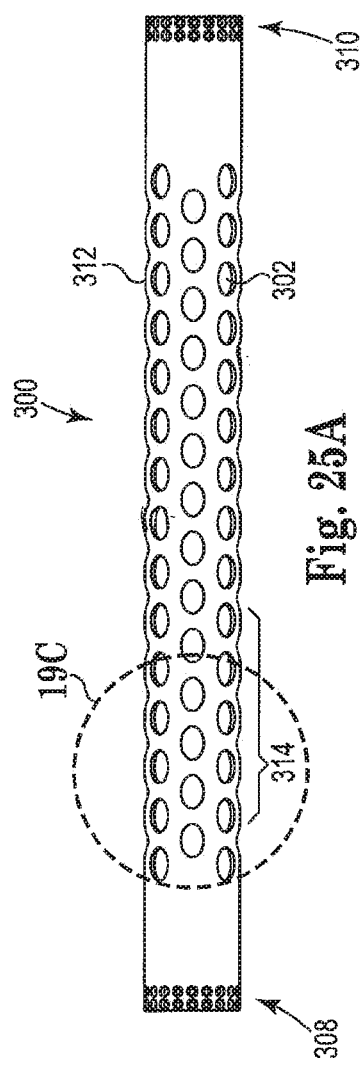
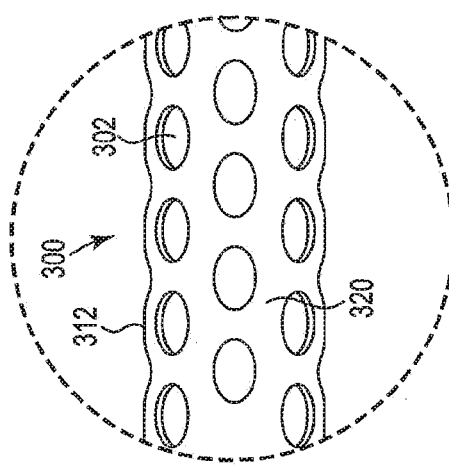

IMPLANTABLE PENILE PROSTHESIS

PRIORITY CLAIM

The present patent application is a continuation of U.S. patent application Ser. No. 14/430,844, filed Mar. 24, 2015, which is a U.S. national stage application under 35 U.S.C. 371 of international Application No. PCT/US2013/062131, filed Sep. 27, 2013, which in turn claims the benefit of U.S. Provisional Patent Application having U.S. Ser. No. 61/706, 468, filed Sep. 27, 2012, entitled "IMPLANTABLE PENILE PROSTHESIS", the disclosures of which are incorporated herein by reference in their entireties.

FIELD OF THE INVENTION

The present application is generally directed to an expandable sleeve component of an implantable penile prosthesis, to a prosthesis containing the sleeve, and to related methods of preparation and use. More specifically, the present application is directed to an implantable penile prosthesis having a cylindrical polymeric (e.g., extruded, molded, etc.) sleeve for controlling cylinder expansion upon placement of the prosthesis within a corpus cavernosum and expansion during use.

BACKGROUND

Implantation of an implantable penile prosthesis (IPP) is a common surgical procedure for treating erectile dysfunction and other penile ailments. Typically, an IPP comprises at least one inflatable cylinder connected to a pump with an integrated reservoir containing a quantity of fill liquid. In other versions, an IPP can alternatively comprise an inflatable cylinder connected by a pump to a separate reservoir for holding the quantity of till liquid. Commercial IPP devices are available under the trade names AMBICOR and AMS 700 from American Medical Systems of Minnetonka, Minn. The entire prosthesis assembly is implanted into the patient's body with the inflatable cylinder being placed in the corpus cavernosum and the pump being placed within the scrotum. The reservoir can also be placed within the scrotum or placed elsewhere within the pelvic region. To operate the IPP, the pump is actuated to transfer fill liquid from the pump into the inflatable cylinder to fill and pressurize the inflatable cylinder.

Conventional inflatable cylinders for IPPS operate by filling the typically hollow inflatable cylinders with a pressurized fill liquid to simulate an erection. The inflatable cylinders are generally defined by an inner tube and an outer tube, wherein the inner tube generally includes the reservoir that receives the pressurized fill liquid so as to transform from a flaccid to an erect state simulating an erection. The outer tube generally functions as a containment member for the inner tube and is used to prevent fluid migration out of the inflatable cylinder in the event of a structural failure of the inner tube.

To further limit the potential for structural failure of the inner tube, conventional inflatable cylinders include an elastic fabric sleeve placed over the inner tube so as to be positioned between the inner tube and the outer tube. In a relaxed state, the elastic fabric sleeve generally fits snugly over the inner tube. Upon introduction of the pressurized fill liquid into the inner tube, the inner tube extends to an erect state and expands in girth, whereby the elastic fabric sleeve is also caused to expand in girth. As the girth of the elastic fabric sleeve increases, the elastic fabric sleeve resists expansion and applies pressure to the inner tube. This pressure helps to prevent the inner tube from expanding beyond a desired limit so as to reduce the potential for failure of the inner tube. When the pressurized fill liquid is to be removed from the inner tube, the elastic fabric sleeve applies pressure that helps to vent and force the pressurized fill liquid from the inner tube such that the inner tube and the elastic sleeve return to their normal, uninflated state. The elastic sleeve is frequently constructed from elastic materials such as those commercially available under the trade names Spandex and Lycra.

A potential disadvantage of the elastic sleeve is that over time and following numerous expansion cycles, the potential exists for the elastic fabric to begin wearing and creating weak spots in the elastic sleeve, such as at locations of a fold. When such wear occurs and weak spots are formed, the potential exists for the inner tube to swell and potentially burst at such a weak spot. This can result in a potential aneurysm where the pressurized inflation fluid is able to escape the inflatable cylinder and to be introduced into the corpus cavernosum. As such, it would be advantageous to have an improved sleeve design that reduces the potential for aneurysm.

SUMMARY OF THE INVENTION

Following are described implantable penile prostheses and components thereof, a particular component being an expandable polymeric sleeve that can be placed to surround an inner inflatable body (e.g., tube or cylinder).

In various embodiments, the expandable polymeric sleeve can be formed of an elastic polymer or an elastic polymer having patterned fenestrations. The polymeric sleeve may be prepared by any method, such as by molding (e.g., injection molding), 3-D printing, die casting, extrusion, or extrusion and laser etching, laser cutting, punching, and the like. Such a pattern-cut or formed expandable polymeric sleeve can be constructed of a polymer material to provide a lattice of repeated cells or fenestrations. Unlike woven or knitted conventional expandable sleeves used in previous implantable penile prostheses, an expandable sleeve as described can be in the form of a homogeneous unitary construct.

A sleeve as described can include a polymeric tube having flexible cylindrical sidewalls between two opposed ends. The sidewalls may be fenestrated or non-fenestrated (solid). According to certain embodiments the sidewalls include fenestrations formed by various lateral, longitudinal, diagonal, linear, non-linear, or otherwise oriented or shaped elastic or in-elastic sidewall structures between the two ends. Fenestrations may be of any geometry and may repeat a pattern of one or more shapes of the same size or different sizes. A fenestration may be round or rounded, circular, square, diamond-shaped, rectangular, triangular, or of any other regular or irregular shape. The sidewall structures are polymeric, non-woven and non-knitted, and may be elastic or inelastic.

An exemplary IPP according to the present invention addresses the aneurysm risks of conventional designs through the inclusion of an expandable polymeric sleeve (e.g., which may be molded) to support and strengthen an inner inflatable body, e.g., tube. The polymeric sleeve is generally snugly positioned over the inner inflatable body (e.g., tube) and is positioned between the inner body and an outer body (e.g., outer tube). The polymeric sleeve generally comprises a cylindrical tube defined between a first end and a second end.

In some embodiments, a plurality of sidewall structures in the form of multiple longitudinal support members extend along a tube length between the first and second ends. A plurality of sidewall structures in the form of lateral shaped rib members are positioned between the adjacently located longitudinal support members. In these embodiments, each rib member can include at least one shaped, non-linear expansion portion capable of expanding and lengthening in-elastically from a non-expanded (relaxed) state to an expanded state. In some embodiments, an expansion portion can define an S-shaped expansion portion, a U-shaped expansion portion, a V-shaped expansion portion, or the like. When pressure is applied from within the expandable sleeve, the plurality of expandable shaped rib members can expand (lengthen) to define an expanded circumferential diameter defining an expanded sleeve in the expanded state that exceeds a non-expanded circumferential diameter when in the normal non-expanded state. Following removal of pressure applied within the molded polymeric sleeve, the ribs transition back to the relaxed disposition and the sleeve returns to the non-expanded state.

According to certain examples, sidewalls of the expandable sleeve in a relaxed disposition can comprise fenestrations between longitudinally-extending spokes generally extending in a direction between ends of the sleeve, and lateral ribs generally extending laterally between and connecting the spokes. The ribs may be shaped or linear; if shaped, ribs can be in-elastically extendable laterally and deformed to lengthen and allow the cross-sectional size of the sleeve to expand, e.g., allowing the girth and diameter of the sleeve to increase. A shaped rib that can in-elastically extend laterally may be of a non-linear shape, such as a crooked (cornered), chevron-shaped, curved (e.g., of a waveform such as sinusoidal, U-shaped (having a single curve), S-shaped (having two opposing curves), V-shaped, or any other shape that can be lengthened in-elastically. Optionally, any such shaped rib can also be lengthened elastically after being fully lengthened in-elastically.

According to other examples, sidewalls of an expandable polymeric sleeve in a relaxed disposition can comprise fenestrations between longitudinally-extending linear spokes generally extending in a direction between the opposing ends of the sleeve, and lateral, linear, elastic ribs generally extending laterally between and connecting the spokes. The linear elastic ribs can be elastically lengthened laterally to allow the cross-sectional size of the sleeve to expand, e.g., allowing the girth and diameter of the sleeve to increase.

According to still other examples, sidewalls of an expandable sleeve in a relaxed disposition can comprise fenestrations between diagonally-extending linear or non-linear ribs generally extending diagonally in a direction between ends of the sleeve. Two sets of counter-directional diagonally-extending ribs may extend between the ends in opposite directions and the same trajectory (the same angle of the slant), connecting to or crossing each other at intersections to create a crossing pattern that produces fenestrations that include a diamond-shaped feature. The diagonal ribs, optionally shaped or linear, can be extended laterally (elastically or in-elastically) to lengthen and allow the cross-sectional size of the sleeve to expand, e.g., allowing the girth and diameter of the sleeve to increase.

Exemplary sleeves can provide a prosthesis that, when placed in a patient, exhibits mechanical properties that highly mimic those of a penis in a flaccid condition; these mechanical properties may be improved relative to comparable previous penile prostheses such as those that include a conventional fabric-type (e.g. Spandex) sleeve. Mechanical properties of a penis having implanted cylinders as described, with a polymeric sleeve, can be very similar to properties of an anatomical flaccid penis. Additionally, these and other examples of polymeric sleeves as described can exhibit improved wear resistance relative to implants made with a conventional fabric-type sleeve. A fabric-type sleeve can be susceptible to mechanical bending and kinking when in a deflated and flaccid state; excessive such bending or kinking during use produces mechanical wear of the fabric sleeve at the location of the bending or kinking. Polymeric sleeves as described herein can have less tendency to suffer from such bending or kinking, or can be more durable in the event of such bending or kinking, and therefore exhibit improved durability and resistance to wear relative to implants made with a conventional fabric-type sleeve.

Any of the polymeric expandable sleeves can be prepared of an elastic material, for example a thermoplastic elastomeric polymer. These embodiments of the sleeve can exhibit properties of hardness (e.g., as measured by durometer), flexibility, modulus, elongation, etc., and other properties of elastomeric polymers, and these properties can be selected to result in a sleeve that is useful for a penile prosthesis or that preferably produces a penile prosthesis that exhibits highly suitable or advantageous mechanical properties (as a penile prosthesis) and wear properties. As an example, polymers (e.g., thermoplastic elastomeric polymers) of a polymeric sleeve have been identified to include those that exhibit a durometer in a range from 50 to 85, e.g., 50 to 70, or from 55 to 65, on the Shore type A scale.

In one aspect, the present invention is directed to a molded polymeric sleeve for use in constructing an IPP. Generally, the molded polymeric sleeve of the present invention supports and strengthens an inner tube to eliminate the wear issues and potential aneurysm risks associated with elastic sleeves used in currently available IPP's. Generally, the molded sleeve comprises a cylindrical body having a plurality of spoke members extending between a first end and a second end. Along an outer periphery of the cylindrical body, a plurality of flexible ribs extends between and connects adjacent spoke members. Each flexible rib can comprise an s-shaped body that is capable of transitioning from a relaxed disposition to an extended disposition in response to pressure applied internal to the cylindrical body. When pressure is applied within the cylindrical body, the molded sleeve expands to a maximum diameter wherein the flexible ribs attain the extended disposition and further expansion of the molded sleeve is prevented. Upon removal of the internal pressure, the flexible ribs retract such that the diameter of the molded sleeve decreases to a minimum diameter.

In another aspect, the present invention is directed to an IPP comprising inflatable cylinders constructed with a molded sleeve. Generally, an IPP of the present invention includes a pump, a length of tubing and a pair of inflatable cylinders. Each inflatable cylinder generally comprises an outer tube, an inner tube, a fluid reservoir, a front tip, a rear tip, and a fluid flow block, wherein the molded sleeve is placed over the inner tube and limits the maximum expansion of the inner tube as it is filled with fluid to create an erection. Generally, the molded sleeve includes a plurality of flexible ribs positioned along an outer peripheral surface defined by the molded sleeve, wherein the flexible ribs are capable of transitioning between a relaxed disposition and an extended disposition in response to pressure applied by the inner tube. When the flexible ribs achieve the extended disposition, further expansion of the molded sleeve and consequently, the inner tube is prevented so as to reduce the potential for aneurysm.

In yet another aspect, the present invention is directed to a method for reducing aneurysm risks associated with IPP's. Generally, the method can comprise fabricating an inflatable cylinder including a molded sleeve positioned over an inner tube. The method can further comprise manipulating a pump to transfer fluid from a fluid reservoir into the inner tube. The method can further comprise expanding the molded sleeve in response to pressure applied from within by the inner tube such that a plurality of flexible ribs on the molded sleeve are caused to transition from a relaxed disposition to an extended disposition. The method further comprises resisting further expansion of the inner tube as the flexible ribs reach the extended disposition and apply generally equivalent support about the whole of the inner tube. The method can further comprise manipulating the pump to transfer fluid from the inner tube back to the fluid reservoir, whereby a spring constant in each flexible rib causes the molded sleeve to return to a relaxed disposition about the inner tube.

In one aspect, the invention relates to an implantable penile prosthesis that includes: an elongate inflatable inner body defining an inflatable chamber, the inflatable chamber in fluid communication with a source of pressurizing fluid; and an expandable polymeric sleeve located along a length of an outer surface of the inner body. The expandable polymeric sleeve is extends between a first end and a second end, and is expandable.

In another aspect the invention relates to a method of simulating a natural erection with a penile prosthesis adapted to be implanted in a corpus cavernosum. The method includes: providing an implantable penile prosthesis as described herein; and controlling an increase in diameter of the inner body upon inflation by adapting the expandable polymeric sleeve to allow the inner body to increase in diameter to an inflated inner body diameter that is not more than 180 percent of a filled and non-pressurized inner body diameter.

In another aspect the invention relates to a method of improving a performance property of a penile prosthesis adapted to be implanted in a corpus cavernosum. The method includes: providing an implantable penile prosthesis as described herein; and increasing a thickness of a sidewall of the polymeric sleeve, or increasing a dimension of a sidewall structure of the polymeric sleeve, to improve a performance property.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be more completely understood in consideration of the following detailed description of various embodiments of the invention in connection with the accompanying drawings, in which:

FIG. 8 is a detailed side view of a flexible rib in an extended disposition.

FIGS. 12 through 21 show embodiments of expandable sleeves as described.

FIGS. 12A, 12B, and 12C through 20A and 20B, FIGS. 24A, 24B, and 24C, and FIGS. 25A, 25B, and 25C, show embodiments of expandable sleeves as a side view, end view, and detail view, respectively.

Figure 1:
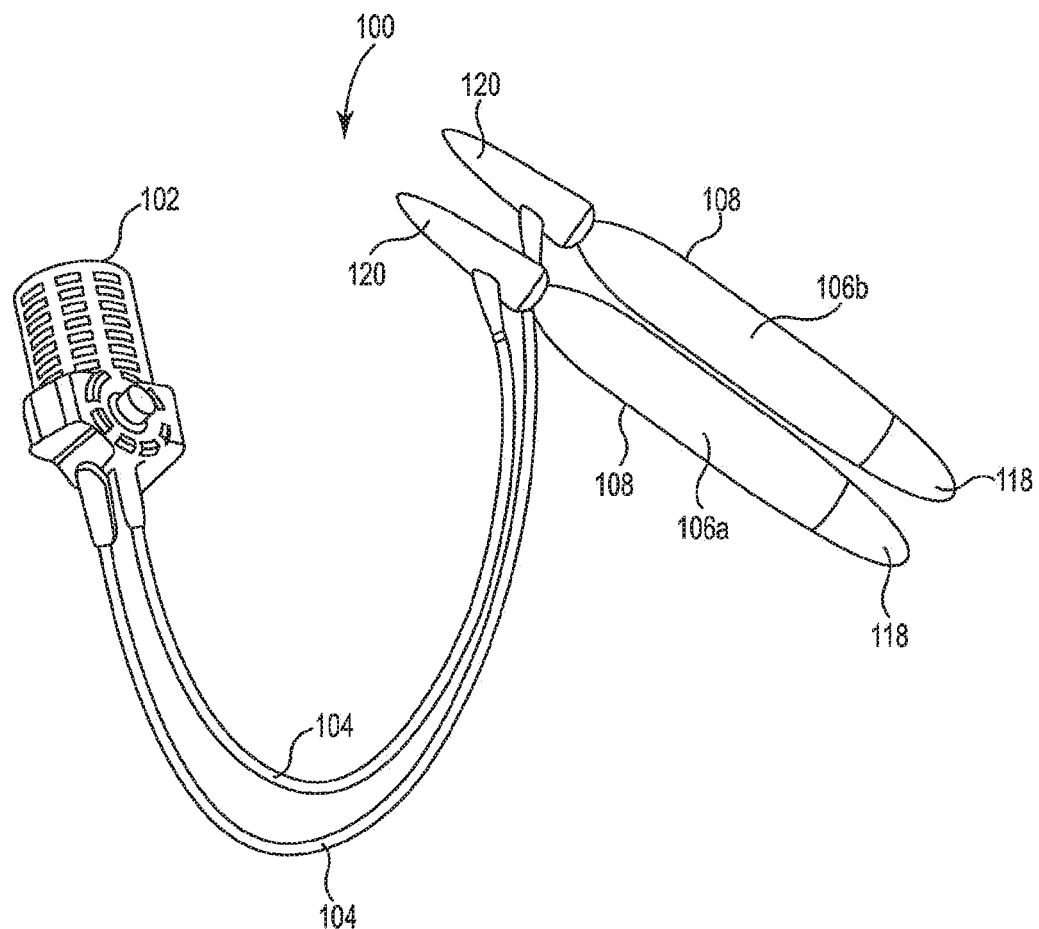
FIG. 1 is a perspective view of an Implantable Penile Prosthesis of the prior art.

While the invention is amenable to various modifications and alternative firms, specifics thereof have been shown by way of example in the drawings and will be described in detail. It should be understood, however, that the intention is not to limit the invention to the particular embodiments as described. On the contrary, the intention is to cover all modifications, equivalents, and alternatives falling within the spirit and scope of the invention as defined by the appended claims.

DETAILED DESCRIPTION

Various types and sizes of implantable penile prostheses are available for treatment of erectile dysfunction. A typical penile prosthesis includes at least one pair of inflatable cylinders, each of the pair being designed to be implantable in one of the corpus cavernosa. The penile prosthesis further includes a pump external to the cylinder for pressurizing the cylinder. The pump is typically connected to the cylinder through tubing near a proximal end of the cylinder. Each cylinder has a fluid tube connected thereto. A pump, typically disposed in the scrotum or abdomen, is connected to a reservoir, which may be at any of various locations. The cylinders are inflated as fluid is pumped from the reservoir, and are deflated as fluid is transferred back to the reservoir. This inflation and deflation allows the patient to control whether his penis is erect or flaccid. An example of such penile prosthesis is the AMS 700™ inflatable penile prosthesis manufactured by American Medical Systems, Inc.

Penile prostheses that can include a sleeve about an inner inflatable body may include features as described in previous patent documents, such as U.S. Pat. Nos. 3,954,102; 4,424,807; 5,263,981; 4,651,721; 6,346,492; 6,733,527; and U.S. Patent Publication 2008/0139880; all of which are incorporated herein by reference. A prosthesis may include a combination of features such as a pair of cylinders, a valve and pump assembly, a fluid reservoir, and intercommunicating flexible tubing or conduits. The entire device can be arranged to be surgically implanted in the body with the two cylinders being disposed within the penis, with the combination valve and pump assembly disposed in either the abdominal cavity or in the scrotum.

The cylinders are arranged for surgical implantation in corpus cavernosum and are constructed to mechanically expand the corpora cavernosa to produce a functional erection without the necessity for the corpora cavernosa to be engorged with blood. The cylinders are readily deflatable to enable the penis to become flaccid when an erection is no longer sought. The cylinders are placed within the corpora cavernosum by surgically preparing a passageway therein. The passageways can be formed by any conventional surgical technique used for prior art penile implants. The passageways can be of any suitable shape. Each passageway can extend down a substantial portion of the length of the associated corpus cavernosum from a point adjacent the glans penis to a point adjacent the scrotum.

Each of the inflatable cylinders implantable in a corpus cavernosum can include an inflatable inner body formed of a flexible polymer such as silicone rubber, an expandable sleeve about the body, and an outer body. Each inflatable cylinder is of generally cylindrical shape with two opposed ends that may be rounded or domed. A distal end of the cylinder can be arranged to be located adjacent the glans penis when the cylinder is located within the passageway with the proximal end located adjacent the root of the penile shaft close to the scrotum. Each cylinder includes an opening or access port to the interior thereof, typically located adjacent the proximal end of the cylinder.

Each cylinder can be arranged to be filled with a fluid, such as water, through its access port, to cause the cylinder to expand longitudinally, as well as radially. Because each cylinder is located in a respective passageway in a corpora cavernosa, the expansion of the cylinder causes concomitant expansion of the corpora cavernosa from its minimal volume (its "flaccid volume") to an increased volume.

Exemplary steps of operating these and similar prostheses are known, and may include the following. The bulb is squeezed (e.g., through the skin of the scrotum) whereupon liquid from the reservoir is forced through tubing and to access ports of each inflatable cylinder. Thus, the cylinders begin to fill beyond the partially filled state. The pump bulb may be squeezed several times to effect a full erection. In this regard, each time the pump bulb is squeezed, more water is forced into the cylinders. Release of the pump or bulb does not allow water to return to the reservoir, e.g., due to a valve. Thus, each time the bulb is resqueezed, additional water is forced into the cylinders. This action causes the cylinders to expand from a flaccid condition to the fully filled or erect condition. As long as the valve prevents water in the cylinders from flowing back to the reservoir, the cylinders remain in their fully filled state and the erection is maintained. When it is desired to render the penis flaccid, a release mechanism at the valve can be actuated to allow water to flow out of the cylinder and into the reservoir, for example under the natural pressure caused by the resiliency of the fibrous envelope on the cylinders. Other prostheses and implantation methods are disclosed in U.S. Pat. Nos. 7,169,103; 6,929,599 and 7,066,878, all of which are incorporated herein by reference in their entireties.

Figure 2:
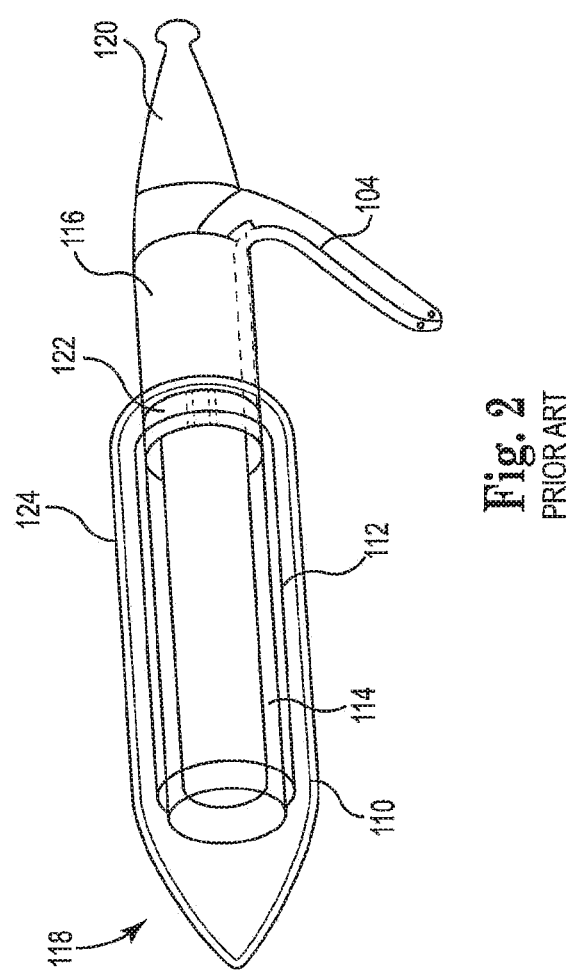
FIG. 2 is a partially hidden view of an inflatable cylinder of the prior art.

As illustrated in FIGS. 1 and 2, a conventional implantable Penile Prosthesis (TPP)) 100 of the prior art can comprise a pump 102, a length of tubing 104 and a pair of inflatable cylinders 106a, 106b. Each of the cylinders 106a, 106b can comprise a cylindrical body 108 including an outer tube 110, an elastic sleeve 112, an inner inflatable body (e.g., inner tube) 114, a fluid reservoir 116, a front tip 118, a rear tip 120, and (preferably) a fluid flow block 122. Elastic sleeve 112 may be an elastic mesh fabric such as Spandex or another tubular fabric sleeve extending about an outer surface of the inner inflatable body. Generally, the outer tube 110 and inner tube 114 are manufactured of suitable medical grade polymers that provide for structural reliability. In some embodiments, the outer tube 110 and inner tube 114 can be manufactured of materials such as, for example, silicone or polyurethane as well as various types of rubber, neoprene, nylon, PVC, polystyrene, polyethylene, polypropylene and other biocompatible polymers known to one of ordinary skill.

Referring again to FIGS. 1 and 2, an outer wall of outer tube 110 is generally in direct contact with the lumen of a patient's corpus cavernosum when implanted. Outer tube 110 generally couples to the front tip 118 and rear tip 120 to define an enclosure 124 that encloses the elastic sleeve 112, inner body (e.g., tube) 114, fluid reservoir 116, and fluid flow block 122. Enclosure 124 generally defines a closed system, when implanted, relative to the corpus cavernosum. In alternate versions, reservoir 116 may be located adjacent to pump 102, abdominally, or elsewhere.

In operation, a user manipulates a valve on pump 102 to direct fluid stored within the fluid reservoir 116 into inner inflatable body 114 of cylinders 106a, 106b, As inner inflatable body 114 of each cylinder 106a, 106b is filled with fluid, each cylinder 106a, 106b generally assumes an inflated and rigid condition. The user can subsequently manipulate the valve on pump 102 to evacuate the fluid from the inner tube 114 of each cylinder 106a, 106b and return the fluid to the fluid reservoir 116, whereby the cylinders 106a, 106b assume a flaccid condition.

Presently described are inventive expandable polymeric sleeves that can be used in an implantable penile prosthesis. The sleeves can be useful as a sleeve component of an implantable penile prosthesis as a replacement for previous sleeve designs, such as previous sleeve components constructed of elastic fabric material. The polymeric sleeve can be incorporated into a penile prosthesis in a manner similar to a fabric sleeve, located about an outer surface of an inflatable inner body. The resulting prosthesis can be implanted and used in similar manners. The polymeric sleeve, in conjunction with a pump and other structural components of an inflatable cylinder component of the prosthesis, can be designed to provide operational limits to the inflated size and inflated pressure of an inflated cylinder. In combination, a pump component and a cylinder component, including an expandable polymeric sleeve, can be designed to allow for an inflatable cylinder that includes a filled inner inflatable body that is filled but not pressurized, is filled and at an ambient pressure (about 0 pounds per square inch, gauge), to exhibit a "non-pressurized" length and diameter. To produce an erection, an inflated inner body may be pumped with water to a pressure in a range of from about 12 to 20 pounds per square inch gauge (psig), e.g., from about 15 to 20 psig. To avoid over-expansion and risk of aneurism, the inflatable inner body (surrounded by an expandable sleeve as described) can be adapted to exhibit a maximum length dimension when inflated that is from 100 percent to 125 percent (e.g., from 105 or 110 percent, to 125 percent) of a length of the non-inflated ("non-pressurized") inner body (e.g., the inflatable inner body exhibits a 0 to 25 percent increase in length upon inflation, e.g., an increase of from 5 or 10 to 25 percent); the inflatable inner body can also be designed to exhibit a maximum diameter when inflated that is from 150 percent to 180 percent (e.g., from 155 to 175 percent) of a diameter of the non-inflated ("non-pressurized") inflatable inner body (e.g., the inner body exhibits a 50 to 80 percent increase in diameter upon inflation, e.g., an increase of from 55 to 75 percent).

In certain embodiments the expandable polymeric sleeve can be made to include fenestrations such as patterned cells, to provide desired expandability (elastic, non-elastic, or both) of the sleeve in lengthwise and lateral directions. The fenestrations can be formed as part of an expandable sleeve prepared by any one or more of molding, die casting, laser etching, laser cutting, extruding, punching, 3-D printing, and the like. The fenestrated expandable sleeve can be constructed of a polymer material to provide fenestrations located along and about the sleeve, such as to exhibit a lattice of patterned and optionally repeated fenestrations. Unlike woven or knitted conventional fabric-type sleeves used in previous implantable penile prostheses, an expandable polymeric sleeve as described can be in the form of a polymeric sheet material in the form of a tube, the tube including continuous polymeric sidewalls defining optional fenestrations as openings in the sidewalls. The polymeric material can be more efficiently used to produce the expandable sleeve, relative to fabric sleeves, and can be manufactured in a manner that provides for wider or thicker polymeric structures at locations of the sleeve that require greater strength (and less expandability) or greater wear resistance, and narrower or thinner polymeric structures at locations of the sleeve that require greater expandability.

An expandable polymeric sleeve may be made of any polymeric material, such as a polymeric material that is essentially in-elastic (in the instance of sleeves having shaped sidewall structures), or a polymeric material that is elastic or elastomeric (in the instance of sleeves having shaped sidewall structures or linear sidewall structures). Each type of polymer is well known and many examples are commercially available. In-elastic polymers are those the exhibit little or no elasticity; examples include certain polyolefins such as polypropylene and its copolymers, nylon, polyester, polyamides, and the like.

Examples of elastomeric polymers that can be suitable for use in a polymeric sleeve as described include thermoplastic elastomeric polymers. Thermoplastic elastomers (TPE), sometimes referred to as thermoplastic rubbers, include polymeric compositions that may be polymeric, copolymeric, or a mixture of two types of polymer or copolymer such as plastic (e.g., thermoplastic) polymer and a rubber (elastomeric) polymer. A thermoplastic elastomer exhibits both thermoplastic and elastomeric properties. In contrast to elastomers that are cured or thermoset (i.e., can be irreversibly cured upon heating or radiation), thermoplastic elastomeric polymers do not thermoset but are thermoformable, meaning that the polymer becomes softened, pliable, and moldable above a specific temperature and can return to a solid state upon cooling to below that temperature. Thermoformable polymers may be melted and processed by extrusion and molding, e.g., injection molding, such as to form an expandable polymeric sleeve as described herein, and also by processes such as blow molding, thermoforming, and heat welding. Thermoplastic elastomers may be considered to exhibit properties that include the ability to be stretched to moderate elongation and, upon the removal of stress, return to something close to an original shape; the ability to be processed as a melt at elevated temperature and solidify at lower temperatures; and a preferred absence of significant creep.

Examples of thermoplastic elastomers include polymeric compositions known as styrenic block copolymers, polyolefin blends, elastomeric alloys, thermoplastic polyurethanes, thermoplastic copolyester, and thermoplastic polyamides. Examples of commercial thermoplastic elastomers include VersaFlex™ (polyurea), Dynaflex® (styrene block copolymer), Kraton® (styrene-butadiene block copolymer), Arnitel® TPE copolyester elastomer, Solprene® (styrene-butadiene-styrene block copolymer), among others.

Examples of polymeric sleeves can be made of a continuous, uniform, and homogenous polymeric material to the exclusion of non-polymeric materials, non-extruded materials, or non-molded materials. Polymeric sidewalls may contain no no-woven, threaded, fibrous, knitted structures, but may be continuous and homogenous polymeric material that may be extruded or molded. Examples of polymeric sleeves may contain up to 100 percent (by weight) extruded or molded polymer (e.g., thermoplastic elastomeric polymer), e.g., 100 percent extruded or molded polymer, greater than 98 or 99 percent extruded or molded polymer, such as at least 40, 50, 60, 70, 80, 90, 95, or 99 weight percent extruded or molded polymer based on the total weight of the polymeric sleeve. Alternately or in addition, a polymeric sleeve may contain at least 40, 50, 60, 70, 80, 90, 95, or 99 weight percent thermoplastic elastomeric polymer based on the total weight of the polymeric sleeve.

A polymeric sleeve as described can be in the form of a polymeric tube having cylindrical, continuous polymeric sidewalls and optional fenestrations between two opposed ends. The sidewalls may include openings (fenestrations) may be continuous without interruptions in the form of any openings (non-fenestrated, or solid). The sidewalls may be of a uniform thickness or varying thickness along a length or circumference of the polymeric sleeve. According to certain embodiments the sidewalls include fenestrations defined between various lateral, longitudinal, diagonal, linear, non-linear, or otherwise oriented or shaped elastic or in-elastic sidewall structures extending and defining a matrix in the sidewalls between the two ends. Fenestrations may be of any geometry, may repeat a pattern of one or more shapes of the same size or different sizes, or may be otherwise shaped and sized to allow the expandable polymeric sleeve to expand and contract when used as described in a penile prosthesis. A fenestration may be round or rounded, circular, oval, square, sinusoidal, diamond-shaped, rectangular, triangular, or may exhibit any other regular or irregular shape. The sidewalls are polymeric and preferably continuous (disregarding the fenestrations); shaped, i.e., non-linear sidewall structures may be elastic or in-elastic.

According to certain examples, sidewalls of the expandable sleeve in a relaxed disposition can include fenestrations between a set of sidewall structures referred to as spokes and ribs; multiple spokes generally extend in a longitudinal direction between the opposed ends of the sleeve; lateral ribs generally extend laterally between and connect the longitudinally-extending spokes. The ribs can be elastically or in-elastically extended (lengthened) (or both) and deformed to allow the cross-sectional size of the sleeve to expand, e.g., allowing the girth and diameter of the sleeve to increase. A shaped rib is a rib that is not a simple linear form but that includes at least one corner or curve and that can lengthen in-elastically; a shaped rib may be of any non-linear shape such as a crooked (cornered or zig-zagged), chevron-shaped, curved such as a waveform that may be sinusoidal, U-shaped (having a single curve), S-shaped (having two opposing curves), or any other non-linear shape that can be lengthened in-elastically. Optionally, any such shaped rib can also be lengthened elastically after being fully lengthened in-elastically. A non-shaped rib is a linear rib that does not include a corner or curve; a non-shaped rib can be extended (i.e., lengthened) elastically.

In more detail, certain examples of sidewalls of an expandable sleeve in a relaxed disposition can have fenestrations between longitudinally-extending linear spokes generally extending in a direction between the opposing ends of the sleeve, and lateral shaped (non-linear) ribs generally extending laterally between and connecting the spokes. The non-linear, shaped ribs can be in-elastically lengthened laterally by transitioning from a relaxed disposition that exhibits its shaped (non-linear) form, to an extended disposition in which the rib is substantially linear; the shape has been substantially removed by lengthening the rib by in-elastic shape-changing deformation. The in-elastic lengthening of the shaped ribs allows the cross-sectional size of the sleeve to expand, e.g., allowing the girth and diameter of the sleeve to increase. The length can also increase, e.g., by elastic lengthening of the spokes. Optionally, in-elastically lengthened shaped ribs may be capable of exerting pressure back onto an inflated inner body to assist in deflation. Also optionally, after in-elastic lengthening, the shaped rib may further extended elastically; the elastically lengthened shaped ribs may also be capable of exerting pressure back onto an inflated inner body to assist in deflation.

According to other examples, sidewalls of an expandable sleeve in a relaxed disposition can have fenestrations between longitudinally-extending linear spokes generally extending in a direction between the opposing ends of the sleeve, and lateral linear ribs generally extending laterally between and connecting the spokes. The linear ribs can be elastically lengthened laterally to a stretched or extended disposition, in which the cross-sectional size of the sleeve is expanded, e.g., the girth and diameter of the sleeve are increased. The elastically lengthened linear ribs in the extended disposition may be capable of exerting pressure back onto an inflated inner body to assist in deflation.

According to still other examples, sidewalls of an expandable sleeve in a relaxed disposition can have fenestrations between diagonally-extending linear or non-linear ribs generally extending diagonally in a direction between ends of the sleeve. Two sets of diagonally-extending ribs may extend between the ends in opposite directions and at the same trajectory (the same angle of the slant relative to a longitudinal axis of the sleeve), connecting to or crossing each other to create a diagonally-crossing pattern that produces fenestrations that include diamond-shaped features. The diagonal ribs can be extended laterally (elastically or in-elastically) to an extended disposition in which the diagonal ribs are lengthened and the cross-sectional size of the sleeve is expanded, e.g., the girth and diameter of the sleeve are increased. Elastically-lengthened linear diagonal ribs may be capable of exerting pressure back onto an inflated inner body to assist in deflation of the inner body. Optionally, in-elastically lengthened shaped diagonal ribs may be capable of exerting pressure back onto an inflated inner body to assist in deflation. Also optionally, after in-elastic lengthening, shaped diagonal ribs may be further extended elastically; the elastically lengthened shaped diagonal ribs may also be capable of exerting pressure back onto an inflated inner body to assist in deflation.

Various embodiments of expandable polymeric sleeves are shown and described herein. Examples of various sleeves may be formed or patterned using a polymer molding process (e.g., injection molding) to create an integral non-woven, non-knitted, continuous (other than fenestrations) polymeric expandable sleeve; alternately, examples of integral non-woven, non-knitted, continuous (other than fenestrations) polymeric expandable sleeves may be formed starting with a polymeric tube having sidewalls in the form of a solid and continuous polymeric sheet or film, by forming apertures in the sidewalls via laser cutting, die cutting, stamping, etching, or the like.

The length, width, and other dimensional characteristics of the polymeric sleeve can vary somewhat over a range of dimensions useful to surround an elongate inflatable body of an implantable penile prosthesis. A thickness of the sidewall of the tube may be any useful thickness to provide one or more of a desired expandability, elasticity, and resistance to wear; exemplary polymeric sleeves may have a uniform or non-uniform thickness along the length and about the circumference, in a range from 0.010 to 0.020 inch, e.g., from about 0.012 to about 0.016 inch.

A pattern of fenestrations, e.g., repeated fenestrations, in a sidewall generally form between sidewall structures in the form of a lattice, which may be considered to include longitudinal members (e.g., spokes), lateral members (e.g., ribs), diagonal members (e.g., ribs or diagonal ribs). The ability to mold, form, or cut the sleeve to produce sidewall structures of nearly endless varieties of linear, curved, cornered, or sinusoidal configurations provides a polymeric sleeve that can perform as a resilient, durable, expandable and optionally elastic polymeric sleeve in a penile prosthesis. For example, a polymeric sleeve as described can perform as well as or better than previous such sleeves prepared from fabric, such as spandex; but the polymeric sleeve as described herein can be more simple and potentially cheaper to produce by a method of molding, injection molding, or extruding and cutting or etching, etc. Additionally, increased strength or wear resistance, or increased or decreased expandability, can optionally be achieved at local regions of a polymeric sleeve by increasing a thickness or width of sidewall structures of a polymeric sleeve at desired locations along a length of or about a circumference of a polymeric sleeve, relative to other locations of the sleeve; the various useful methods available for preparing the polymeric sleeve allow for the preparation of a sleeve with a non-uniform thickness or sidewall structures of non-uniform thickness or width, resulting in localized increased wear resistance, strength, or uniformity of dimensions upon expansion, along a length or about a perimeter.

In certain embodiments, sidewall structures include longitudinal spokes connected by curved sinusoidal shaped ribs. The thickness, length, width, and separation of the sidewall structures (e.g., spokes, ribs) can be modified as desired along a length or circumference of a sleeve to produce a polymeric sleeve with any desired surface area, fenestration density, wear resistance, expandability, etc. Thickness and width of the sidewall structures may be uniform or varied along a length or circumference of a sleeve; the sidewall structures can have uniform or variable widths or thicknesses, can be tapered, can include apertures, or can define fenestrations of any desired shapes or patterns, e.g., sinusoids, squares, rectangles, circles, diamonds, elliptical, triangular, elbowed, straight-edged, or other simple or complex shapes and patterns.

The design of the sidewall structures, e.g., shape, thickness, width, etc., can be configured differently at different portions of a polymeric sleeve, for example to produce desired (increased or decreased) strength, expandability, flexibility, and wear resistance of the polymeric sleeve at different locations of the polymeric sleeve, e.g., at different locations along a length of the polymeric sleeve or at different locations about a circumference of the polymeric sleeve. For instance, a width or thickness of a sidewall structure may be increased at a location at which increased strength or resistance to expandability is desired; a width or thickness of a sidewall structure may be decreased at a location at which decreased strength or resistance to expandability is desired.

Figure 3:
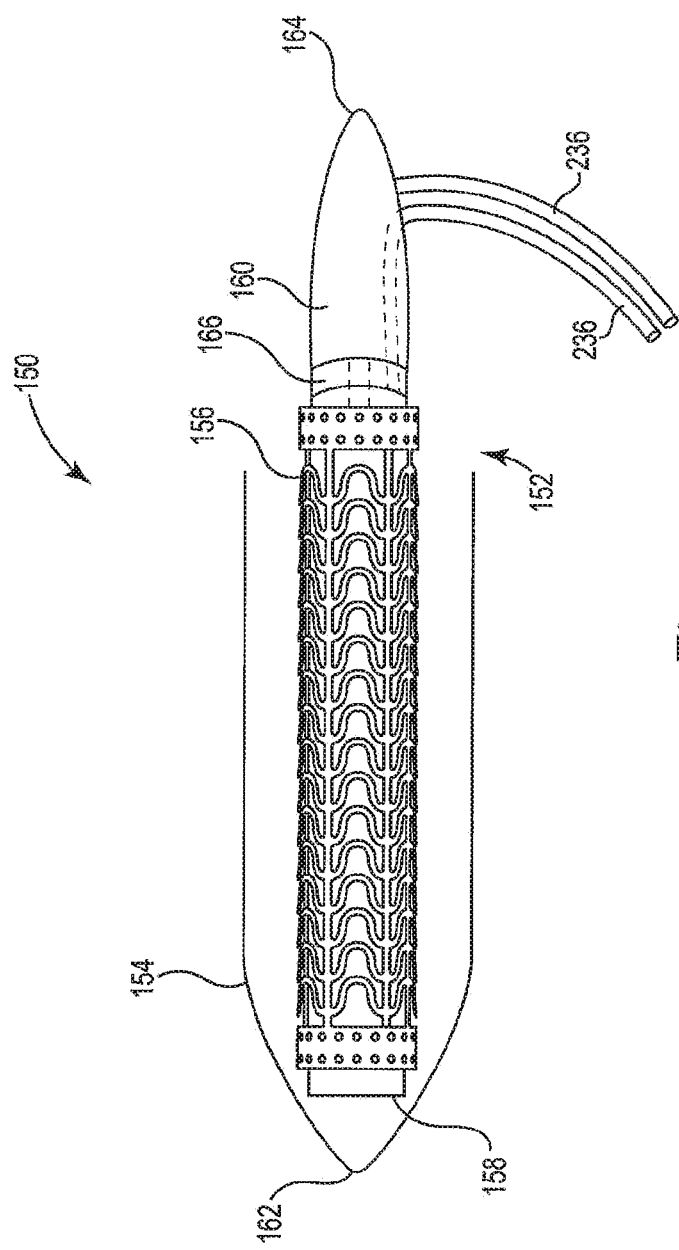
FIG. 3 is a partially hidden view of an inflatable cylinder according to an embodiment of the present invention.

Referring now to FIG. 3, an inflation cylinder 150 of the present invention can comprise a cylindrical body 152 defined by an outer tube 154, a polymeric (e.g., molded) sleeve 156, an inner inflatable body (e.g., tube) 158, an optional fluid reservoir 160, a front tip 162, a rear tip 164 and an optional fluid flow block 166. Generally, the outer tube 154 and inner inflatable body (e.g., tube) 158 are manufactured of suitable medical grade polymers that provide for structural reliability. In some embodiments, the outer tube 154 and inner tube 158 can be manufactured of materials such as, for example, silicone or polyurethane as well as various types of rubber, neoprene, nylon, PVC, polystyrene, polyethylene, polypropylene and other biocompatible polymers known to one of ordinary skill in the art.

Figure 4:
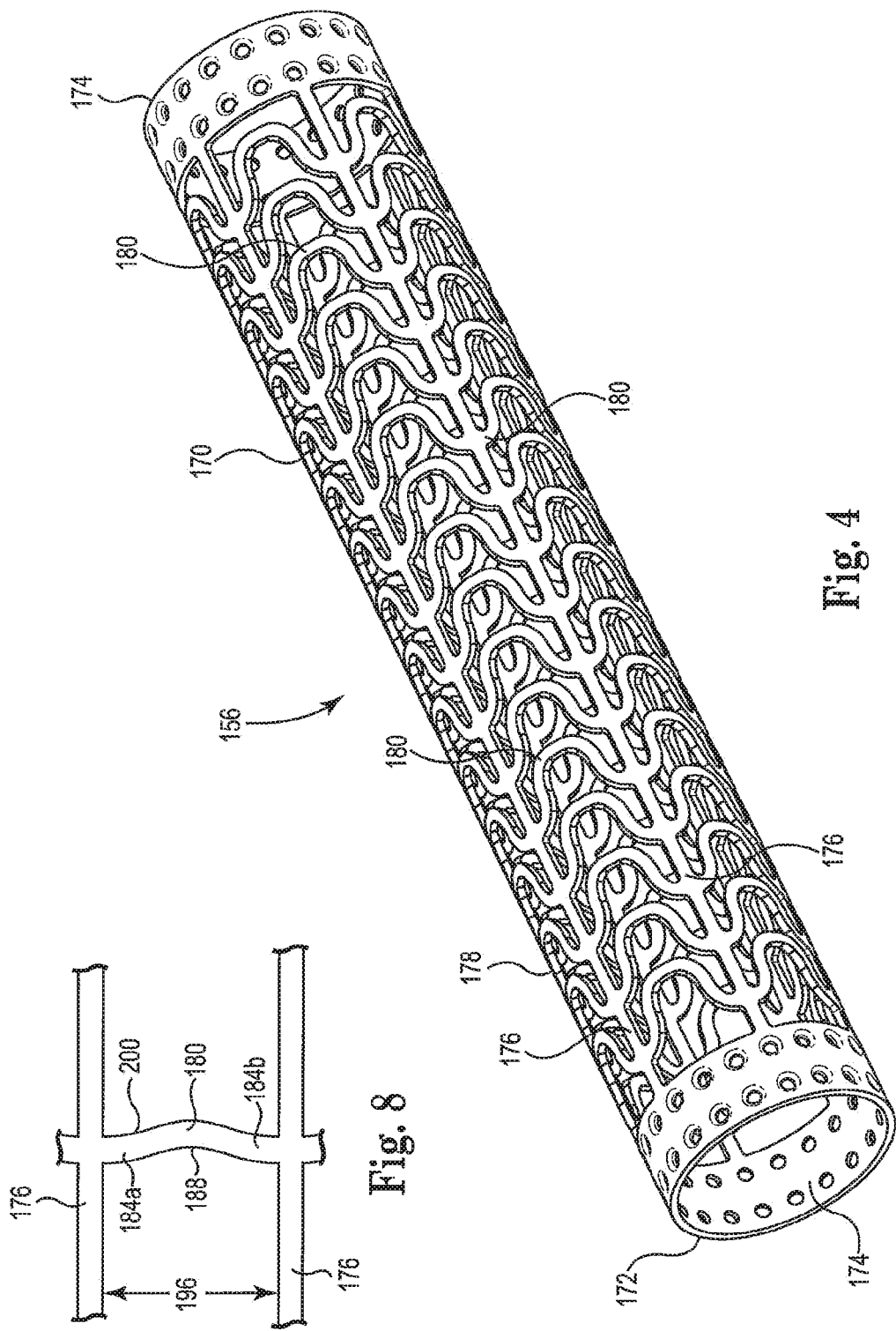
FIG. 4 is a perspective view of a molded sleeve according to an embodiment of the present invention.
Figure 5:
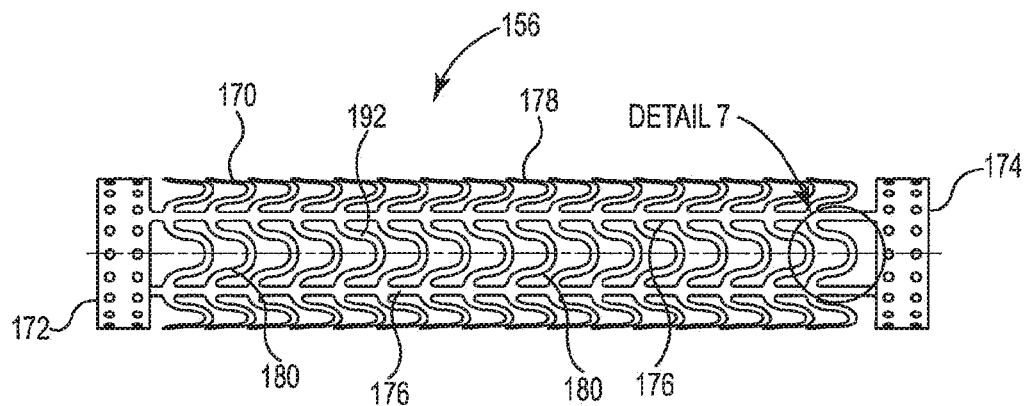
FIG. 5 is a side view of the molded sleeve of FIG. 4.
Figure 6:
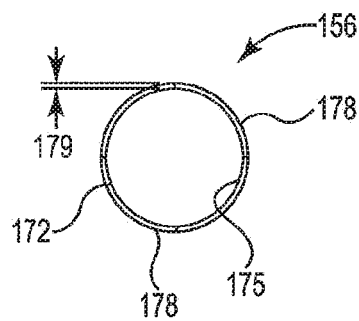
FIG. 6 is an end view of the molded sleeve of FIG. 4.

As seen in FIGS. 4, 5 and 6, polymeric (e.g., molded) sleeve 156 generally comprises a cylindrical sleeve body 170 having a first end 172 and a second end 174. Cylindrical sleeve body 170 generally has sidewalls that include inner wall 175 and external wall 178 defining a sidewall or body thickness 179. A plurality of spoke members 176 extend between and connect the first end 172 and the second end 174. Extending between adjacent spoke members 176 along the circumference of external wall 178 are a plurality of flexible shaped ribs 180. Sleeve 156 can be fabricated using suitable molding or extrusion and cutting techniques. In one preferred embodiment, sleeve 156 can be injected molded of a suitable medical grade polymer such as, for example, polypropylene or a thermopolymer elastomer.

Figure 7:
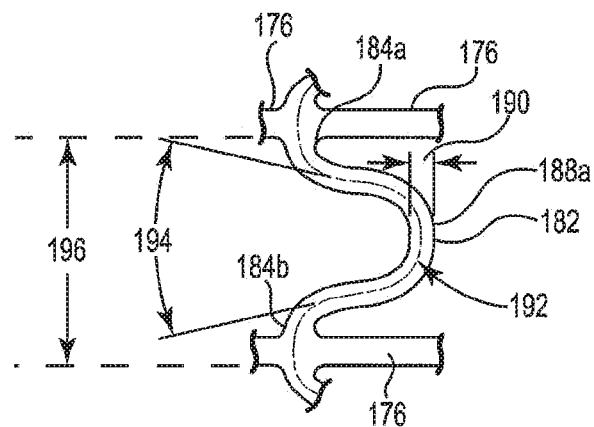
FIG. 7 is a detailed side view of a flexible rib taken at Detail 7 of FIG. 5.
Figure 9:
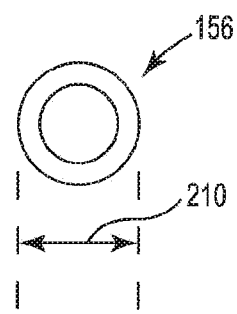
FIG. 9 is an end view of the molded sleeve of FIG. 4 in a relaxed disposition.

As illustrated in FIG. 7, each flexible rib 180 generally comprises a curved U-shaped rib body 182 having a pair of rib connecting ends 184a, 184b, and an arcuate rib span 188. Each flexible rib 180 generally has a rib width 190 that can remain generally consistent throughout the length of the rib body between ends 184a and 184b. As illustrated in FIGS. 4, 5 and 9, flexible rib 180 is illustrated in a relaxed disposition 192 wherein a leg angle 194 defined between the central axis of adjacent legs of U-shaped rib body 182 is less than about 90 degrees, and more preferably, about 25 degrees. In relaxed disposition 192, a spoke distance 196 is defined between adjacent spoke members 176 as measured about the external wall 178.

When sleeve 156 is expanded, due for example to pressure applied from within cylindrical sleeve body 170, each flexible rib 180 transitions to an extended disposition 200 as shown in FIG. 8. In extended disposition 200, leg angle 194 increases and generally approaches 180 degrees, such that flexible rib 180 approaches a generally linear or axial member 202 in which it becomes difficult to distinguish between rib legs 186a, 186b and central rib span 188. In extended disposition 200, spoke distance 196 is increased as compared to the spoke distance 196 in the relaxed disposition 192. A transition between relaxed disposition 192 and extended disposition 200 may be in-elastic, meaning that flexible rib 180 lengthens due to a transition in shape from the U-shape of the relaxed disposition to the linear form of the extended disposition. Optionally, ribs 180 of the extended disposition 200 may additionally lengthen due to reversible elastic deformation or elastic expansion of each rib 180.

Figure 10:
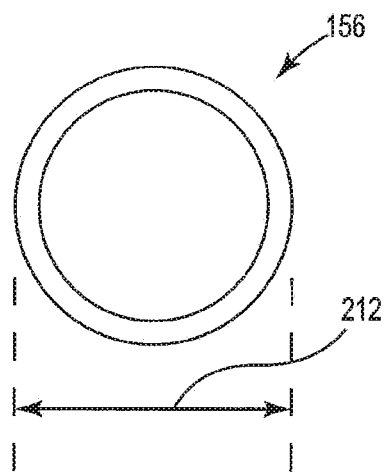
FIG. 10 is an end view of the molded sleeve of FIG. 4 in an extended disposition.

Referring now to FIG. 9, molded sleeve 156 (or 300 as also described herein) generally has a relaxed diameter 210 when the flexible ribs are in the relaxed disposition. Following elastic or in-elastic expansion and lengthening of flexible ribs or other lateral sidewall structures to an extended disposition, polymeric sleeve 156 or 300 has an expanded diameter 212 as shown in FIG. 10 that exceeds relaxed diameter 210.

Figure 11:
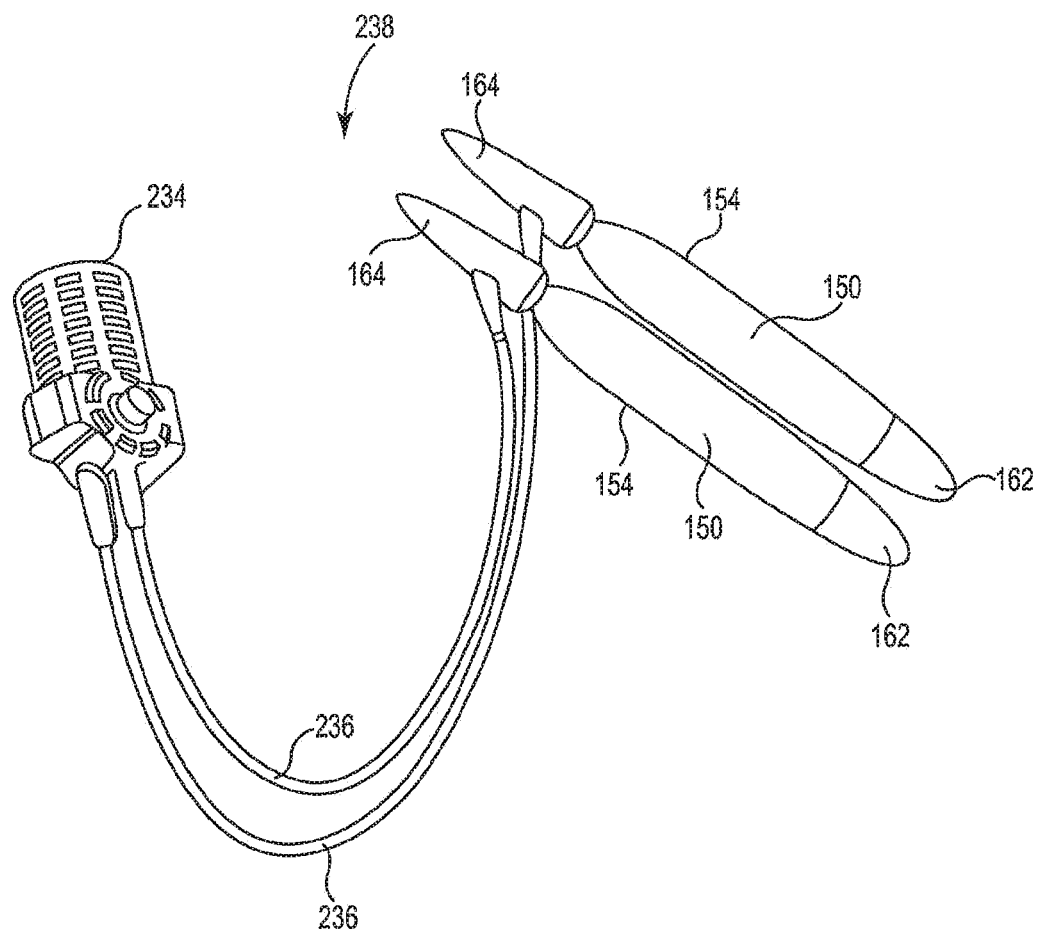
FIG. 11 is a perspective view of an implantable Penile Prostheses according to an embodiment of the present invention.
Figure 19B:
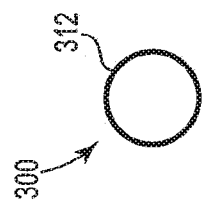
Figure 19A:
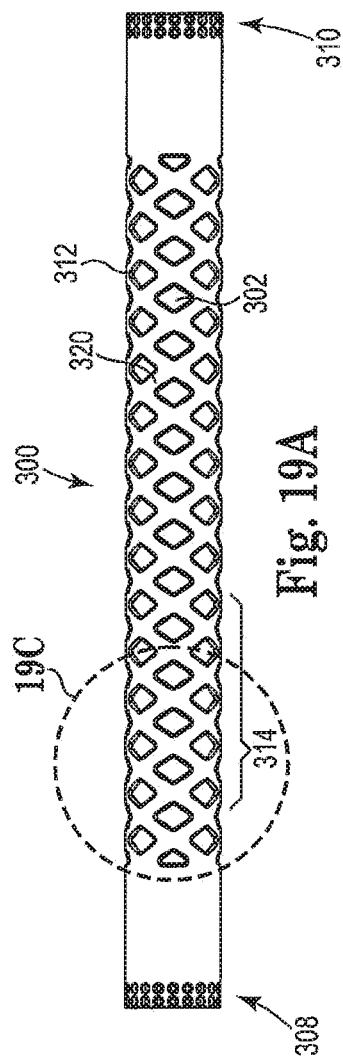
Figure 19C:
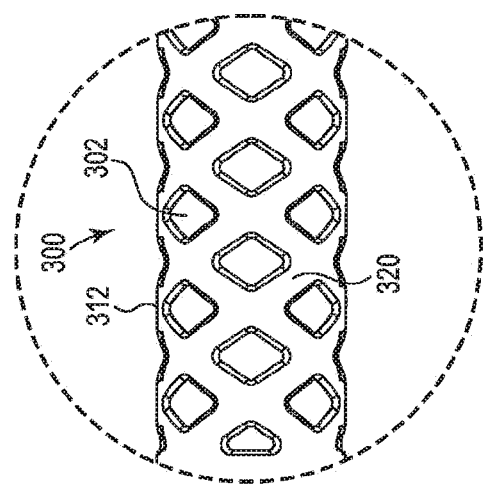

FIG. 11 shows an embodiment of an implantable penile prosthesis that includes an expandable polymeric sleeve 156 (not shown) (alternately a sleeve 300) as described herein.

Some of the preceding description and related figures identify embodiments of expandable sleeves that include non-linear, shaped ribs that allow an expandable sleeve to expand by ribs lengthening in an in-elastic manner to an extended disposition, then also optionally extending elastically beyond the in-elastic lengthening. Alternate embodiments of expandable sleeves include linear (non-shaped) ribs that may be lateral or diagonal relative to a longitudinal axis of a sleeve, and that are elastic, allowing an expandable sleeve to expand with elastic lengthening of ribs or other sidewall structure. Examples are shown at FIGS. 12 through 19. Still other embodiments of expandable sleeves include a sleeve having solid, non-fenestrated elastic sidewalls that may expand laterally, as shown in FIG. 20.

Each of FIGS. 12, 12A, 12B, and 12C, through 17, 17A, 17B, and 17C, shows an expandable polymeric sleeve 300 that includes fenestrations 302, longitudinal spokes 304 and linear elastic ribs 306 making up sidewalls 312, and opposing ends 308 and 310. The size of fenestrations 302 can be as desired, and can vary as shown in the various illustrated embodiments of sleeve 300. The width and thickness of longitudinal spokes 304 as well as linear elastic ribs 306 can also be as desired, and can vary as shown in the various illustrated embodiments of sleeve 300. Not apparent in the illustration, a thickness of sidewalls 312, e.g., spokes 304, ribs 306, or both, can differ at different locations along a length or a circumference of the sidewalls. A length portion 314, for example, may include sidewall structures (spokes, ribs, or both) that are thicker (or wider) than sidewalls structures of the same sleeve at other length-wise locations. As one example, referring to FIGS. 17A and 17C, fenestrations 302a toward opposing ends 308 and 310 are smaller in area compared to fenestrations 302b along a length at a central portion of sleeve 300; also at FIGS. 17A and 17C, linear ribs 306a toward opposing ends 308 and 310 are larger in width compared to linear ribs 306b along a length at a central portion of sleeve 300.

Each of FIGS. 18, 18A, 183, 18C, 19, 19A, 19B, and 19C, shows an expandable polymeric sleeve 300 that includes fenestrations 302 and diagonal ribs 320 and 322 extending as a sidewall structures at an angle, like a spiral, about a longitudinal axis (not shown) of sleeve 300. The size of fenestrations 302 can be as desired, and can vary as shown in the various illustrated embodiments of sleeve 300. The width and thickness of diagonal ribs 320 and 322 can also be as desired and can vary as shown in the various illustrated embodiments of sleeve 300. Not apparent in the illustration, a thickness of sidewalls 312, e.g., spokes 304, ribs 306, or both, can differ at different locations along a length or a circumference of the sidewalls. A length portion 314, for example, may include sidewall structures (spokes, ribs, or both) that are thicker or wider than sidewalls structures of the same sleeve at other length-wise locations.

FIGS. 24A, 243, 24C, 25A, 25B, and 25C show alternate variations of expandable sleeves having oval fenestrations.

The following description refers specifically to FIGS. 3 and 11, and the sleeve embodiment of FIG. 3 having curve-shaped ribs 180; the description is not limited to the sleeve of FIG. 3 and can apply to alternate embodiments of expandable sleeves (e.g., 300) and implantable penile prostheses described herein. Referring now to FIGS. 3 and 11, a polymeric sleeve 156 can be used to construct an inflatable cylinder 150 of an inflatable penile prosthesis. Inflatable cylinder 150 can include outer tube 154, molded sleeve 156 (alternately 300), inner expandable body (e.g., tube) 158, fluid reservoir 160 (alternately located at pump 234), front tip 162, rear tip 164, and optional fluid flow block 166. A pair of inflatable cylinders 150 can be implanted within a patient's corpus cavernosum and operably coupled to a pump 234 by a length of tubing 236 to form an Implantable Penile Prosthesis 238.

In operation, a user can operate Implantable Prosthesis 238 by manipulating the pump 234 to cause fluid to be transferred from a fluid reservoir (e.g., 160) and into inner inflatable body 158. As fluid enters the inner body 158, inner body 158 expands, thereby applying pressure to the inner wall 175 of sleeve 156. As the pressure on inner wall 175 increases, each of the flexible ribs 180 transitions from the relaxed disposition 192 to the extended disposition 200. Each rib body 182 is in direct contact with the inner body 158 and cooperatively assists to allow a desired level of expansion and prevent further expansion of inner body 158 while applying generally equivalent support about the whole of the inner body 158. By preventing expansion of inner body 158 in excess of a desired amount of expansion, and applying uniform support of the inner body 158, potential failure or compromising of the inner body 158 is avoided such that the chances of aneurysm are reduced. When the user subsequently manipulates the pump 234 such that the fluid is returned to the fluid reservoir 226 from the inner tube 224, the pressure applied to inner wall 175 is removed. With the pressure removed, the spring constant of each flexible rib 180 causes the rib legs 186a, 186b to return to the relaxed disposition 192.

Figure 21:
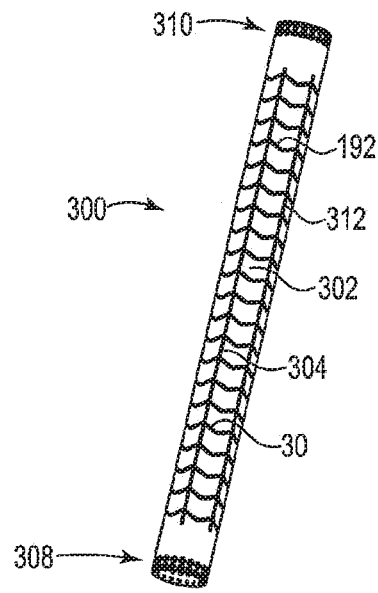
Figure 22:
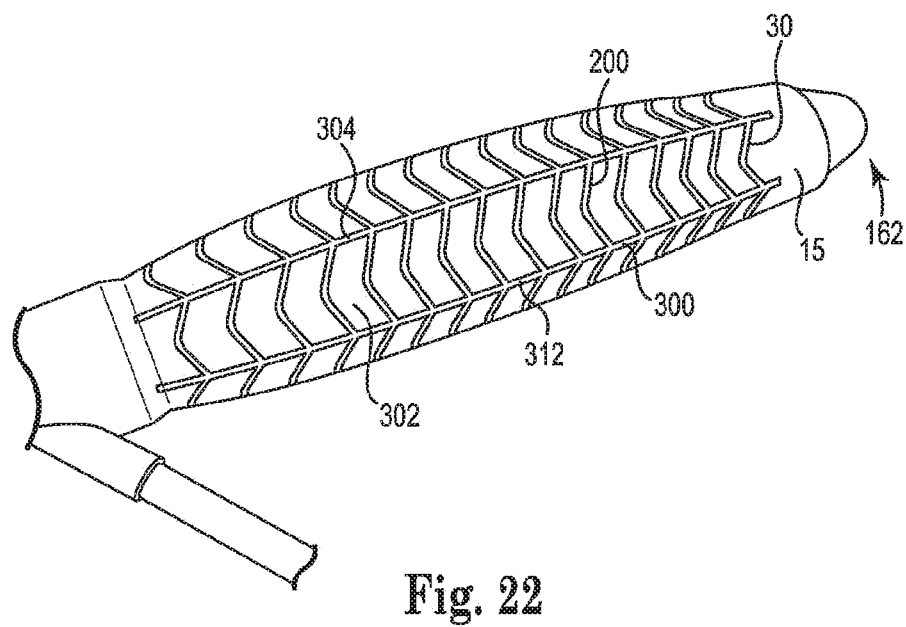
FIG. 22 shows an embodiment of an inner inflatable body and expandable sleeve as described.
Figure 23:
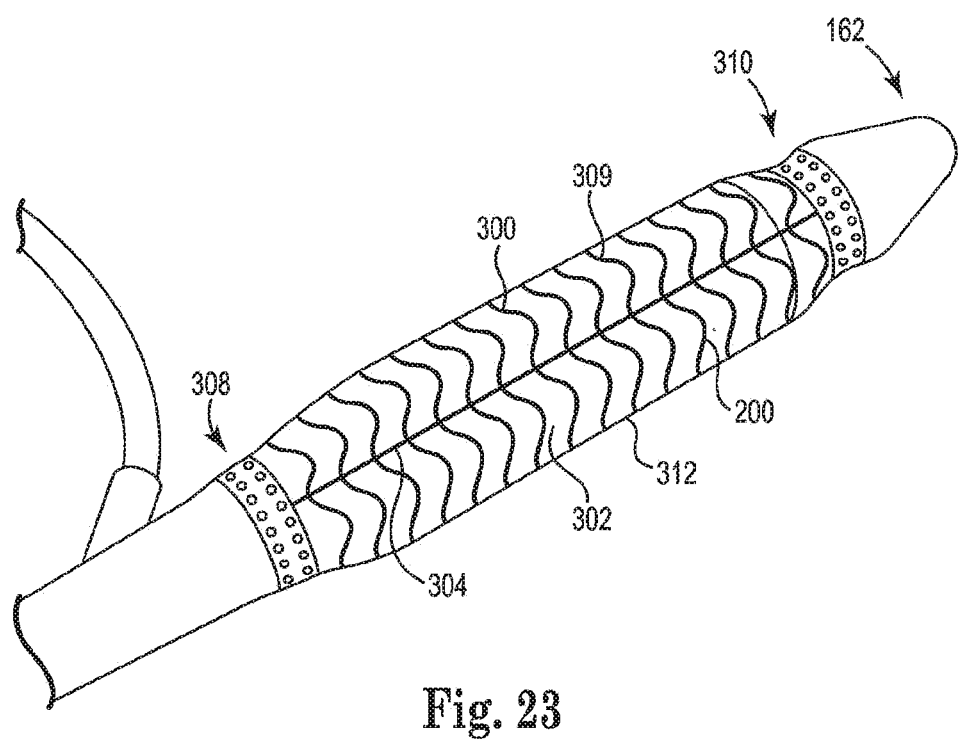
FIG. 23 shows an embodiment of an inner inflatable body and expandable sleeve as described.

FIGS. 21 and 22 show a second embodiment of an expandable polymeric sleeve 300 having shaped (chevron shaped) ribs 307. FIG. 21 illustrates sleeve 300 including shaped ribs 307 in a relaxed disposition 192. FIG. 22 shows sleeve 300 placed about an outer surface of expandable inner body 158, which has been expanded to place pressure on an inner surface or inner wall of sleeve 300, causing shaped ribs 307 to transition to an extended disposition 200 by which shaped ribs 307 have become in-elastically lengthened. FIG. 23 shows an alternate embodiment of a similar combination of inner body 158, about which is disposed sheath 300 having "U-shaped" ribs 309 in an extended disposition 200. The immediately preceding description relates to the operation of an expandable sleeve as described, having shaped ribs that can deform in-elastically to allow expansion of the polymeric sleeve. Alternate sleeve embodiments having non-shaped lateral or diagonal ribs can operate in a similar fashion but based on elastic expansion of the sleeve due to elastic lengthening of the lateral or diagonal ribs. In operation of a prosthesis that includes an expandable sleeve having linear elastic ribs such as described herein and illustrated at any of FIGS. 12 through 19, or a solid elastic sleeve as illustrated at FIG. 20, a user can operate Implantable Penile Prosthesis 238 by manipulating pump 234 to cause fluid to be transferred from a fluid reservoir (e.g., 160) and into inner inflatable body 158. As fluid enters the inner body 158, inner body 158 expands, thereby applying pressure to an inner wall of a sleeve 300 as illustrated at any of FIGS. 12 through 20. As pressure on the inner wall of the sleeve increases, the diameter of the expandable sleeve increases, such as by elastic expansion of a solid sleeve as shown at FIG. 20, or by elastic expansion of lateral or diagonal ribs of a fenestrated sleeve as shown at FIGS. 12 through 19); each of the flexible elastic linear ribs of a fenestrated sleeve transitions from a relaxed disposition to an extended disposition by elastic lengthening. Each rib body is in direct contact with an inner inflatable body and cooperatively assists to allow a desired level of expansion and to prevent further expansion of the inner body beyond a desired level of expansion, while applying generally equivalent support about the whole of the inner body. By preventing expansion of the inner body in excess of a desired amount, and by applying uniform support of the inner body 158, potential failure or compromising of the inner body is avoided such that the chances of aneurysm are reduced.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. An implantable penile prosthesis comprising:
   an elongate inflatable inner body defining an inflatable chamber, the inflatable chamber in fluid communication with a source of pressurizing fluid; and
   an expandable polymeric sleeve located along a length of an outer surface of the elongate inflatable inner body, the polymeric sleeve defining a plurality of openings.

2. The implantable penile prosthesis as recited in claim 1 comprising:
   an inflatable cylinder including:
      an outer tube,
      a front tip, and
      a rear tip; and
   a pump capable of pressurizing the fluid;
   a fluid reservoir in communication with the pump and the inner body, the expandable polymeric sleeve located along a length of an outside of the elongate inflatable inner body and within the outer tube.

3. The prosthesis as recited in claim 2, wherein the polymeric sleeve comprises thermoplastic elastomeric polymer.

4. The prosthesis as recited in claim 3, wherein the polymeric sleeve comprises at least 40, 50, 60, 70, 80, 90, 95, or 99 weight percent thermoplastic elastomeric polymer.

5. The prosthesis as recited in claim 1, wherein the polymeric sleeve comprises at least 40, 50, 60, 70, 80, 90, 95, or 99 weight percent extruded or molded polymer.

6. The prosthesis as recited in claim 5, wherein the polymeric sleeve is elastically expandable.

7. The prosthesis as recited in claim 6, wherein the polymeric sleeve is in-elastically expandable.

8. The prosthesis as recited in claim 7, wherein the polymeric sleeve comprises fenestrations defined by sidewall structures capable of transitioning between a relaxed disposition and an extended disposition.

9. The prosthesis as recited in claim 8, wherein the polymeric sleeve comprises fenestrations defined between longitudinal spokes connected by laterally-extending shaped ribs capable of in-elastically transitioning between a relaxed disposition and an extended disposition.

10. The prosthesis as recited in claim 9, wherein the ribs have a shape selected from at least one of a chevron, an "S" shape, a "U" shape, or a "V" shape.

11. The prosthesis as recited in claim 8, wherein the polymeric sleeve comprises rectangular fenestrations defined between longitudinal spokes and laterally connecting linear ribs, the ribs comprising laterally-extending rectangular bodies capable of extending elastically.

12. The prosthesis as recited in claim 8, wherein the polymeric sleeve comprises diamond-shaped fenestrations defined between diagonally-extending linear ribs, the ribs including diagonally-extending rectangular bodies capable of extending elastically.

13. The prosthesis as recited in claim 6, wherein the polymeric sleeve is non-fenestrated and is capable of extending elastically.

14. The prosthesis as recited in claim 13, comprising:
a pump in fluid communication with the inflatable chamber.

15. The prosthesis as recited in claim 14, wherein the polymeric sleeve has a uniform thickness along a length between a first end and a second end.

16. The prosthesis in recited at claim 14, wherein the polymeric sleeve has non-uniform thickness along a length between a first end and a second end.

17. The prosthesis as recited in claim 14, wherein the polymeric sleeve includes sidewall structures of varying width, thickness, or both.

18. The prosthesis as recited in claim 14, wherein the polymeric sleeve includes sidewall structures of relatively greater width, thickness, or both, at a location of increased wear potential due to bending, kinking, or flexing.

19. A method of simulating a natural erection with a penile prosthesis adapted to be implanted in a corpus cavernosum, the method comprising:
providing an implantable penile prosthesis having an elongate inflatable inner body defining an inflatable chamber, the inflatable chamber in fluid communication with a source of pressurizing fluid, and an expandable polymeric sleeve located along a length of an outer surface of the elongate inflatable inner body, the polymeric sleeve defining a plurality of openings; and
controlling an increase in diameter of the inner body upon inflation by adapting the expandable polymeric sleeve to allow the inner body to increase in diameter to a maximum inflated inner body diameter that is not more than 180 percent of a filled and non-pressurized inner body diameter.

20. The method of claim 19, wherein the inflated inner body exhibits a chamber pressure in a range from about 12 to 20 pounds per square inch (gauge).

* * * * *